United States Patent
Lee et al.

(10) Patent No.: US 12,427,515 B2
(45) Date of Patent: Sep. 30, 2025

(54) INTEGRATED MOLECULAR DIAGNOSIS APPARATUS

(71) Applicant: WIZBIOSOLUTIONS INC., Gyeonggi-do (KR)

(72) Inventors: Kook Nyung Lee, Seoul (KR); Hyun Young Lee, Gyeonggi-do (KR); Sang Gyu Cho, Gyeonggi-do (KR); Dong Ki Hong, Gyeonggi-do (KR); Jeong Hun Cheon, Gyeonggi-do (KR); Joo Sung Kang, Gyeonggi-do (KR); Hye Lim Kang, Gyeonggi-do (KR); Seo Jin Yun, Gyeonggi-do (KR)

(73) Assignee: WIZBIOSOLUTIONS INC., Gyeonggi-do (KR)

(*) Notice: Subject to any disclaimer, the term of this patent is extended or adjusted under 35 U.S.C. 154(b) by 885 days.

(21) Appl. No.: 17/673,629

(22) Filed: Feb. 16, 2022

(65) Prior Publication Data

US 2023/0137860 A1    May 4, 2023

(30) Foreign Application Priority Data

Nov. 3, 2021 (KR) .................. 10-2021-0149875
Nov. 5, 2021 (KR) .................. 10-2021-0151223
Jan. 13, 2022 (KR) .................. 10-2022-0005099

(51) Int. Cl.
*B01L 3/00* (2006.01)
*B01L 7/00* (2006.01)
*C12Q 1/6844* (2018.01)

(52) U.S. Cl.
CPC ............. B01L 3/502 (2013.01); B01L 7/52 (2013.01); *B01L 2200/026* (2013.01); *B01L 2200/0684* (2013.01); *B01L 2200/10* (2013.01); *B01L 2200/16* (2013.01); *B01L 2300/0663* (2013.01); *B01L 2300/0883* (2013.01); *B01L 2300/123* (2013.01); *C12Q 1/6844* (2013.01)

(58) Field of Classification Search
CPC ...... B01L 3/502; B01L 7/52; B01L 2200/026; B01L 2200/0684; B01L 2200/10;
(Continued)

(56) References Cited

U.S. PATENT DOCUMENTS 5,616,301 A * 4/1997 Moser ................. B01L 7/52
                                                      422/562
5,658,531 A * 8/1997 Cope ................. G01N 21/0303
                                                      422/430

(Continued)

FOREIGN PATENT DOCUMENTS

KR      20100001925 U  *  2/2010

OTHER PUBLICATIONS

Translation of KR20100001925U; Feb. 23, 2010 (Year: 2010).*

*Primary Examiner* — Henry H Nguyen
(74) *Attorney, Agent, or Firm* — ZION IP; Byungwoong Park

(57) ABSTRACT

An integrated molecular diagnosis apparatus including a buffer tube into which a sample collection tool collecting a sample is inserted, the buffer preparing a sample solution that contains nucleic acid extracted from the collected sample, a cartridge combined with the buffer tube and supplied with the sample solution, the cartridge transporting the sample solution to a reaction chamber through a fluid channel and performing a nucleic acid amplification reaction, and a diagnosis module main body detachably combined with the cartridge, the diagnosis module main body supplying heat at a predetermined temperature to the reaction chamber, detecting the nucleic acid amplification reaction, and determining whether or not a diagnosis target is present.

22 Claims, 25 Drawing Sheets

(58) Field of Classification Search
CPC ......... B01L 2200/16; B01L 2300/0663; B01L 2300/0883; B01L 2300/123; B01L 3/5029; B01L 2300/023; B01L 2300/0672; B01L 2400/0683; B01L 3/502715; B01L 3/50825; B01L 2300/043; C12Q 1/6844; C12Q 1/701; C12Q 1/6806; A61B 10/0045; A61B 10/02

See application file for complete search history.

(56) References Cited

U.S. PATENT DOCUMENTS

| | | | |
|---|---|---|---|
| 6,454,137 B1* | 9/2002 | Sturk | B65D 47/043 222/481.5 |
| 7,727,480 B2* | 6/2010 | Tajima | B01L 3/5021 422/68.1 |
| 2014/0329329 A1* | 11/2014 | Wong | B01L 3/502753 422/534 |
| 2015/0240300 A1* | 8/2015 | Ansari | C12Q 1/6869 506/38 |
| 2015/0353919 A1* | 12/2015 | Mielke | B01L 3/5029 435/6.12 |
| 2016/0238553 A1* | 8/2016 | Shachar | G01N 27/4145 |
| 2018/0333717 A1* | 11/2018 | Motadel | B01L 3/50825 |
| 2019/0201898 A1* | 7/2019 | Cucchi | B01L 3/502753 |
| 2020/0362397 A1* | 11/2020 | Zhou | C12Q 1/6825 |
| 2021/0086173 A1* | 3/2021 | Samsoondar | B01L 3/502 |
| 2021/0131993 A1* | 5/2021 | Buie | G01N 27/4167 |

* cited by examiner

INTEGRATED MOLECULAR DIAGNOSIS APPARATUS

STATEMENT OF GOVERNMENTAL SUPPORT

Individual Project Number: 1465032760
Project Number: HW20C2068
Government Ministry: Ministry of Health and Welfare
Institution: Korea Health Industry Development Institute
Research Project Title: Disinfection Technology Development Project
Research Project Title: Development of Integrated LAMP-type Molecular Diagnosis
Apparatus for Sample Pretreatment, Capable of Quick Diagnosis on the Spot
Contribution Ratio: 1/1
Project Researcher Institute: WIZBIOSOLUTIONS INC.
Project Period: 2020 Sep. 1~2023 Feb. 28

CROSS REFERENCE TO RELATED APPLICATION

The present application claims priority to Korean Patent Application Nos. 10-2021-0149875, 10-2021-0151223, and 10-2022-0005099 filed Nov. 3, 2021, Nov. 5, 2021, and Jan. 13, 2022, respectively, the entire contents of which is incorporated herein for all purposes by this reference.

BACKGROUND OF THE INVENTION

Field of the Invention

The present disclosure relates to an integrated molecular diagnosis apparatus and, more particularly, to an integrated molecular diagnosis apparatus capable of independently performing a process from pretreatment of a collected sample to molecular diagnosis thereof with a user's involvement being minimized. Furthermore, the integrated molecular diagnosis apparatus is capable of being manufactured in a small size and thus performing point-of-care testing.

DESCRIPTION OF THE RELATED ART

Usually, a molecular diagnostic method directly performs genetic testing of harmful bacteria or viruses. Thus, the molecular diagnostic method has an advantage in precision and more accurate diagnosis of causative organisms of infectious diseases over an immunodiagnostic method. However, a diagnosis procedure is complex because the molecular diagnostic method sequentially performs sample collection, cell destruction, nucleic acid extraction, and nucleic acid amplification. Furthermore, it takes a long time of approximately 30 minutes to 2 hours to obtain a result of diagnosis.

Therefore, research has been conducted on quick pretreatment of a sample in order to shorten a testing time taken for the molecular diagnosis method and to find application in point-of-care testing (POCT). Usually, a pretreatment of sample is to extract nucleic acids (DNA, RNA, and the like) in a cell for amplifying the nucleic acids on a polymerase chain reaction (PCR) process. Specifically, a component that interrupts or suppresses an amplification reaction is removed, and only target nucleic acids are purified to a greater level of purity.

A sample pretreatment method in the related art extracts nucleic acids using a centrifugal separator. However, in recent years, technologies have been developed that automate a sample pretreatment process without using the centrifugal separator. Accordingly, cartridge integrated molecular diagnosis apparatuses that independently perform a process from sample pretreatment to molecular diagnosis have been commercialized.

Usually, the cartridge integrated molecular diagnosis apparatuses control a fluid with a mechanical method, using a valve or a motor in order to transport a sample during a process from the sample pretreatment to the amplification. Therefore, a cartridge structure or a control method is complex. In addition to this method, there is an electrowetting method that is used to control a small volume of fluid. However, an electrode array that is required to complicate manufacturing process is essential, thereby increasing the cost of a cartridge. Furthermore, the reliability of a result of diagnosis is relatively low.

The foregoing is intended merely to aid in the understanding of the background of the present disclosure, and is not intended to mean that the present disclosure falls within the purview of the related art that is already known to those skilled in the art.

SUMMARY OF THE INVENTION

An objective of the present disclosure is to provide an integrated molecular diagnosis apparatus capable of independently performing a process from pretreatment of a collected sample to molecular diagnosis thereof with a user's involvement being minimized. Furthermore, the integrated molecular diagnosis apparatus is capable of being manufactured in a small size and thus performing point-of-care testing.

According to an aspect of the present disclosure, there is provided an integrated molecular diagnosis apparatus comprising: a buffer tube into which a sample collection tool collecting a sample is inserted, the buffer preparing a sample solution that contains nucleic acid extracted from the collected sample; a cartridge combined with the buffer tube and supplied with the sample solution, the cartridge transporting the sample solution to a reaction chamber through a fluid channel and performing a nucleic acid amplification reaction; and a diagnosis module main body detachably combined with the cartridge, the diagnosis module main body supplying heat at a predetermined temperature to the reaction chamber, detecting the nucleic acid amplification reaction, and determining whether or not a diagnosis target is present.

The disclosed technology may have the following effects. However, a specific implementation example of the integrated molecular diagnosis apparatus is not meant to be acquired to achieve all the following effects or only the following effects, and therefore should not be understood as imposing any limitation on the claimed scope of the present disclosure.

An integrated molecular diagnosis apparatus according to an embodiment of the present disclosure can independently perform a process from pretreatment of a collected sample to molecular diagnosis thereof with a user's involvement being minimized. The integrated molecular diagnosis apparatus can be manufactured in a small size, and thus can perform point-of-care testing.

BRIEF DESCRIPTION OF THE DRAWINGS

The above and other objectives, features, and other advantages of the present disclosure will be more clearly understood from the following detailed description when taken in conjunction with the accompanying drawings, in which.

DETAILED DESCRIPTION OF THE INVENTION

Figure 1:
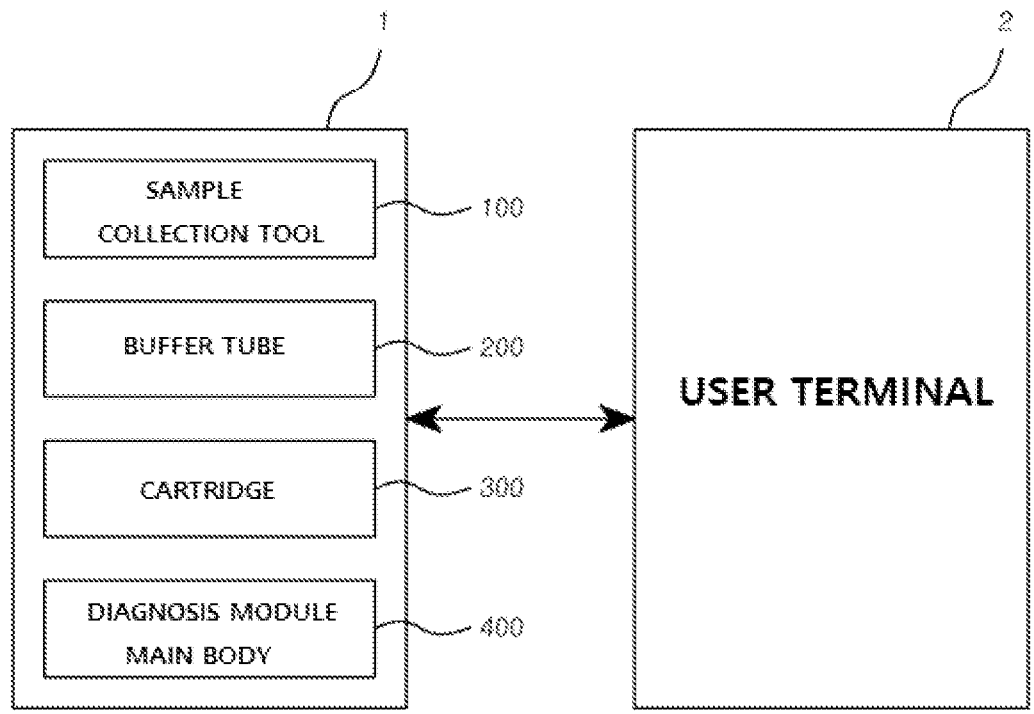
FIG. 1 is a block diagram illustrating an integrated molecular diagnosis system according to a first embodiment of the present disclosure.

An embodiment of the present disclosure will be described below in an exemplary manner in terms of structures and functions. Therefore, the claimed scope of the present disclosure should not be construed as being limited by the embodiment of the present disclosure. That is, various modifications can be made to the embodiment, and the embodiment can take various forms. Therefore, equivalents of the embodiment that can realize the technical idea of the present disclosure should be understood as falling within the scope of the present disclosure. In addition, a specific embodiment is not meant to be required to achieve all the objectives of the present disclosure or all the effects thereof or to achieve only all the effects, and therefore should not be understood as imposing any limitation on the claimed scope of the present disclosure.

The terms used through the present application should be understood as having the following meanings.

The terms "first", "second", and so on are intended to distinguish among constituent elements and therefore should not be construed as imposing any limitation on the claimed scope of the present disclosure. For example, a first constituent element may be named a second constituent element. In the same manner, the second constituent element may also be named the first constituent element.

A constituent element, when described as being "connected to" a different constituent element, should be understood as being connected directly to the different constituent element or as being connected to the different constituent element with a third intervening constituent element interposed therebetween. By contrast, a constituent element, when described as being "connected directly to" a different constituent element, should be understood as being connected to the different constituent element without any third intervening constituent element interposed therebetween. Expressions such as "between" and "directly between" and expressions such as "adjacent to" and "directly adjacent to" that are used to describe a relationship between constituent elements should also be construed in the same manner.

The term used in the present specification, although expressed in the singular, is construed to have a plural meaning, unless otherwise explicitly meant in context. It should be understood that the terms "include", "have", and the like are intended to indicate that a feature, a number, a step, an operation, a constituent element, a component, or any combination thereof is present, without precluding the possible presence or addition of one or more other features, numbers, steps, operations, constituent elements, or any combination thereof.

Identification characters (for example, a, b, c, and so forth) are assigned to steps for convenience of description. The identification characters do not indicate the order of steps. Unless otherwise stated in context, steps may be performed in a different order of steps than in the mentioned order of steps. That is, steps may be performed in the mentioned order of steps. Steps may be performed substantially at the same time and may be performed in reverse order of the steps.

The present disclosure may be realized as computer-readable codes recorded on a computer-readable recording medium. Computer-readable recording media include all types of recording devices on which data readable by a computer system are stored. Examples of the computer-readable recording medium include a ROM, a RAM, a CD-ROM, a magnetic tape, a floppy disk, an optical data storage device, and the like. In addition, codes that are distributed to computer systems connected through a network and are readable by a computer in a distributed manner may be stored on the computer-readable medium and may be executed therefrom.

Unless otherwise defined, each of all terms used throughout the present specification has the same meaning as is normally understood by a person of ordinary skill in the art to which the present disclosure pertains. A term as defined in a commonly used dictionary should be construed as having the same meaning as that in context in the related art and, unless otherwise explicitly defined in the present application, should not be construed as having an excessively implied meaning or a purely literal meaning.

Figure 2:
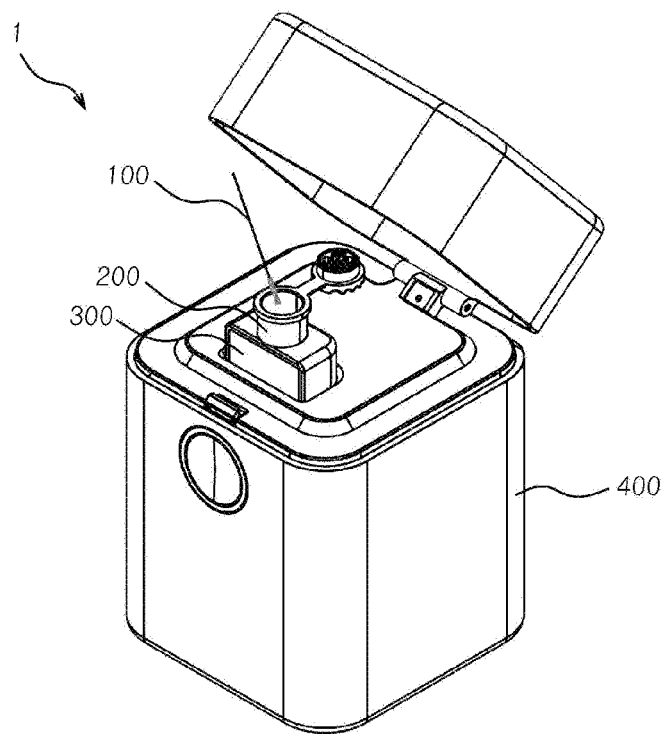
FIG. 2 is a view illustrating an implementation example of an integrated molecular diagnosis apparatus illustrated in FIG. 1.

FIG. 1 is a block diagram illustrating an integrated molecular diagnosis system according to a first embodiment of the present disclosure. FIG. 2 is a view illustrating an implementation example of an integrated molecular diagnosis apparatus illustrated in FIG. 1.

With reference to FIGS. 1 and 2, the integrated molecular diagnosis system according to the first embodiment of the present disclosure may include an integrated molecular diagnosis apparatus 1 and a user terminal 2. The integrated molecular diagnosis apparatus 1 may communicate with the user terminal 2 through a network. The networks here may include wired communication networks, wireless communication networks employing communication standards, such as a wireless LAN, Wi-Fi, Bluetooth, and Zigbee, and various types of mobile communication networks employing communication standards, such as 2G, 3G, 4G, 5G, and LTE.

The integrated molecular diagnosis apparatus 1 may automatically pretreat a sample that is collected from a user subject to diagnostic testing and then is injected thereinto. From the pretreated sample, the integrated molecular diagnosis apparatus 1 may determine in real time whether or not a diagnosis target is present. The diagnosis target according to the present disclosure may be bacteria or virus that cause a respiratory disease. Examples of the diagnosis target may include the bacteria or virus that cause a respiratory disease, such as a respiratory syncytial virus (RSV), a COVID-19, and a delta COVID-19. The integrated molecular diagnosis apparatus 1 may transmit a result of the diagnosis to the user terminal 2.

The integrated molecular diagnosis apparatus 1 may include a sample collection tool 100, a buffer tube 200, a cartridge 300, and a diagnosis module main body 400. In this case, the sample collection tool 100, the buffer tube 200, and the cartridge 300 are disposable, and may be disposed of after use. The sample collection tool 100 collects a sample from the user subject to diagnostic testing. The sample collection tool 100 may collect a sample from a mucous membrane on an inner wall of a nasal cavity or oral cavity of the user subject to diagnostic testing. The sample collection tool 100 may be formed to have a shape for easily collecting a sample from the user subject to diagnostic testing and may be formed of a material for easily collecting a sample from the user subject to diagnostic testing. For example, the sample collection tool 100 may be formed to have the shape of a swab in such a manner as to be insertable into the nasal cavity or oral cavity of the user subject to diagnostic testing.

The sample collection tool 100 is accommodated in the buffer tube 200 into which a buffer solution is pre-injected, for being immersed into the buffer solution. The buffer solution here is obtained by mixing a lysis buffer, which is a buffer solution that is used when breaking a cell membrane, or with micro-particles or the like for improving lysis efficiency. This buffer solution may be pre-injected into the buffer tube 200.

The buffer tube 200 extracts nucleic acid from the sample collected through the sample collection tool 100 and prepares a sample solution. Generally, methods of destroying a cell membrane of a sample include a chemical method of adjusting pH of a buffer solution, a method of heating a buffer solution to a predetermined temperature 60 to 95□ C and thus removing a large protein molecule through protein denaturation, a method of applying a physical impact using an ultrasonic wave, and the like.

A sample containing bacteria or virus that causes a respiratory disease has a relatively smaller number of impurities than blood or other samples. For this reason, according to the first embodiment of the present disclosure, the method of destroying a cell membrane by shaking the buffer tube 200 to apply a physical and chemical impact on a sample is employed. That is, in a state where the sample collection tool 100 is inserted into the buffer tube 200 and where the buffer tube 200 is sealed, the sample collection tool 100 is shaken in such a manner that the buffer solution is together shaken. With this motion, the cell membrane of the sample is destroyed, and thus the nucleic acid may be extracted. The first embodiment of the present disclosure is not limited to this extraction method. At least one of a method of applying a physical impact by heating a buffer solution and a method of applying a physical impact using an ultrasonic wave may be employed together to extract nucleic acid.

The buffer tube 200 may be inserted into the cartridge 300 for being mounted therein and may supply to the cartridge 300 the sample solution from which the nucleic acid is extracted. The buffer tube 200, when inserted into the cartridge 300, may discharge the sample solution to the outside by drilling a hole in the bottom surface of the buffer tube 200. To this end, the buffer tube 200 may be formed of a non-rigid plastic material having excellent chemical resistance. For example, the buffer tube 200 may be formed of polypropylene (PP), polycarbonate (PC), or the like.

The cartridge 300 is combined with the buffer tube 200 and is supplied with the sample solution from the buffer tube 200. The cartridge 300 extracts a fixed amount of sample solution through at least one fluid channel and mixes the extracted amount of sample solution with a pre-injected reagent. Then, the cartridge 300 is supplied with heat at a predetermined temperature from the diagnosis module main body 400 and performs a nucleic acid amplification reaction.

The reagent here serves to detect the diagnosis target by amplifying the nucleic acid contained in the sample and may be pre-injected into the cartridge 300 in a frozen and dry state. The cartridge 300 may be formed of a non-rigid transparent material having excellent chemical resistance. For example, the cartridge 300 may be formed of polypropylene (PP), polycarbonate (PC), acryl, or the like.

The diagnosis module main body 400 may be detachably combined with the cartridge 300. According to a preset operating condition, the diagnosis module main body 400 may supply heat at a predetermined temperature, which is necessary for the nucleic acid amplification reaction, to the cartridge 300. Then, the diagnosis module main body 400 may measure color or a fluorescent magnitude of the sample solution that varies with the nucleic acid amplification reaction and thus may determine whether or not the diagnosis target is present. The operating condition here may be set as a state where the sample solution is mixed with the reagent within the cartridge 300 in preparation for performing the nucleic acid amplification reaction after the cartridge 300 is inserted into the diagnosis module main body 400.

Under the control of the user terminal 2, the diagnosis module main body 400 may communicate with the user terminal 2 to transmit a result of diagnosing the diagnosis target. That is, in the integrated molecular diagnosis apparatus 1 according to the first embodiment of the present disclosure, a procedure in which a user transfers the sample solution into the cartridge 300, and so on are omissible. Thus, a pretreating process of collecting the sample and extracting and amplifying the nucleic acid and a diagnosis process may be independently performed in one apparatus in a state where user's involvement is minimized.

The user terminal 2 may communicate with the integrated molecular diagnosis apparatus 1 to control operation of the integrated molecular diagnosis apparatus 1. The user terminal 2 may display on a screen the result of the diagnosis supplied from the integrated molecular diagnosis apparatus 1. The result of the diagnosis may be displayed as negative or positive. In addition, the user terminal 2 may provide a screen on which the time required for the diagnosis and the result of the diagnosis are displayed. For storage, the user terminal 2 may transmit the place and the date and time of the diagnosis and the like to a database, along with the result of the diagnosis. The database here may be located inside or outside the user terminal 2 and may be managed by a separate server.

The user terminal 2 may be a computing apparatus that is used by a user who uses the integrated molecular diagnosis apparatus 1. For example, the user terminal 2 may be a computing apparatus, such as a smartphone, a tablet PC, or a desktop PC, but is not limited to these apparatuses. An application that is to be executed in conjunction with the integrated molecular diagnosis apparatus 1 may be installed on the user terminal 2.

Figure 3A:
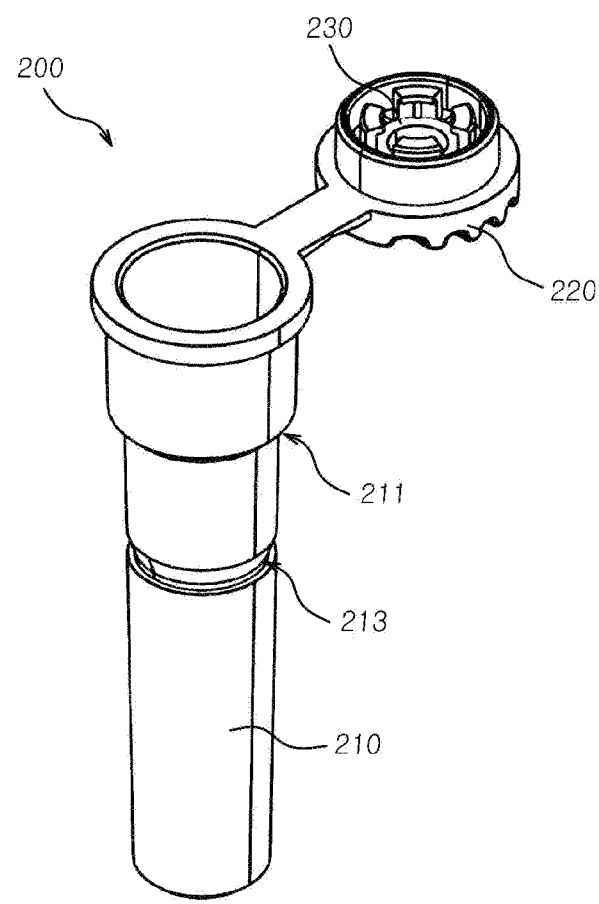
FIGS. 3A to 3C are views each illustrating a buffer tube illustrated in FIG. 1.
Figure 3B:
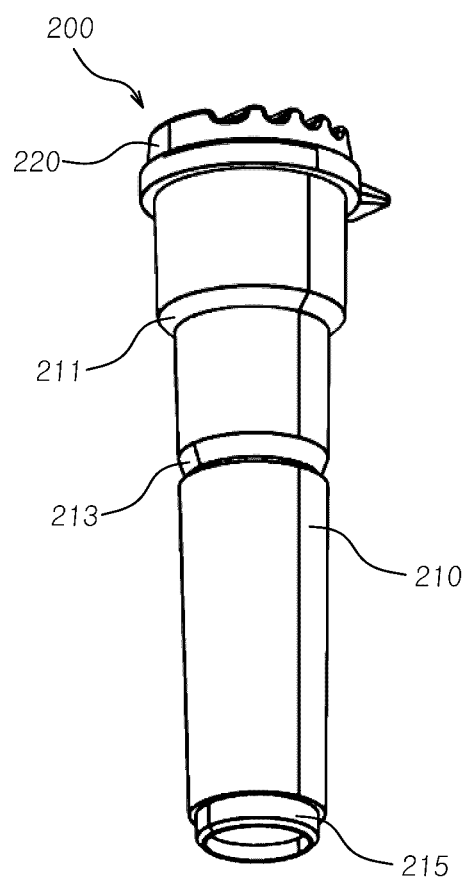
Figure 3C:
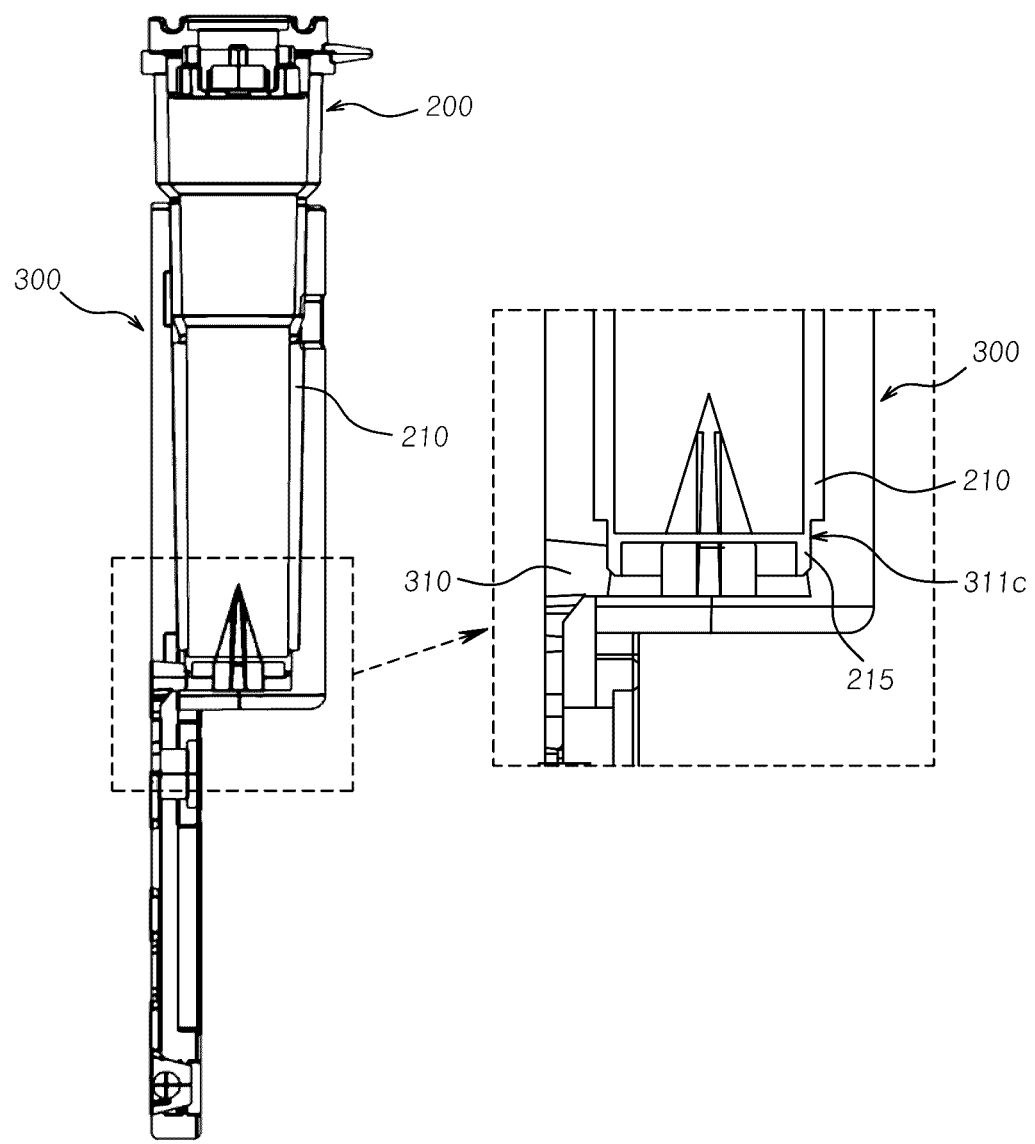
Figure 4A:
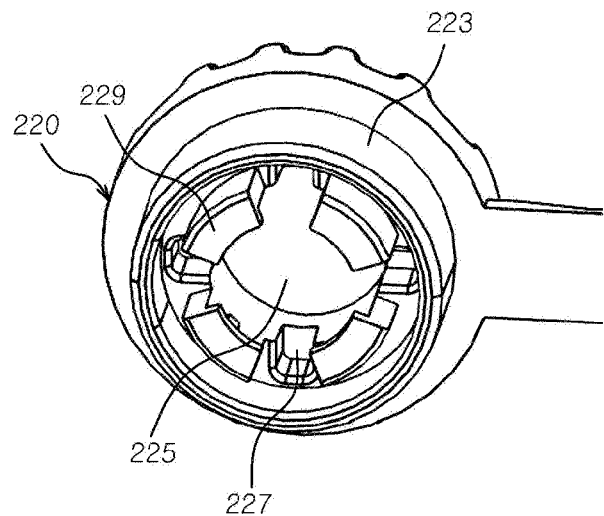
FIGS. 4A to 4C are views each illustrating an opening and closing body illustrated in FIGS. 3A to 3C.
Figure 4B:
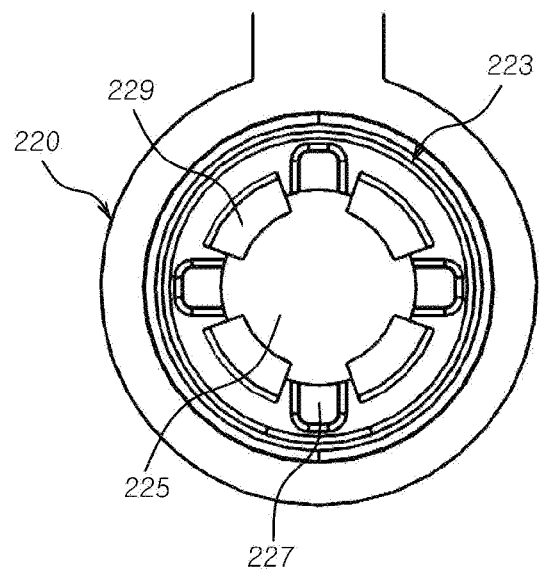
Figure 4C:
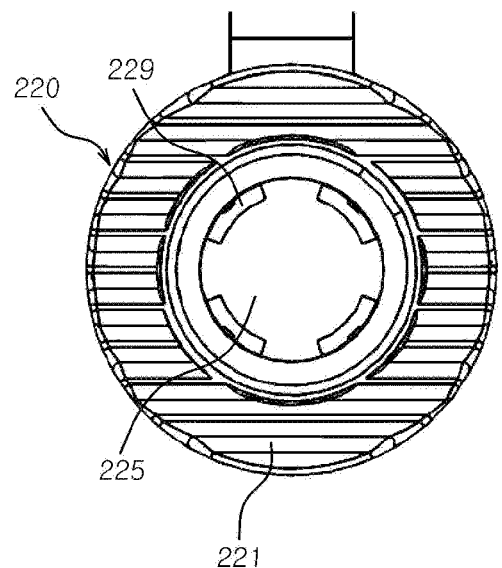

FIGS. 3A to 3C are views each illustrating the buffer tube 200 illustrated in FIG. 1. FIGS. 4A to 4C are views each illustrating an opening and closing body illustrated in FIGS. 3A to 3C. FIG. 3C is a vertically cross-sectional view illustrating a state where the buffer tube 200 in FIG. 1 is combined with a cartridge body illustrated in FIG. 5. FIG. 4B is a bottom view illustrating the opening and closing body illustrated in FIG. 4A. FIG. 4C is a top view illustrating the opening and closing body illustrated in FIG. 4A.

With reference to FIG. 3A, the buffer tube 200 may include a tube body 210, an opening and closing body 220, and an inlet-port plugging member 230. The tube body 210 is formed to have the shape of a cylinder and has an internal space in which the buffer solution is accommodated. The tube body 210 is open at the top. The opening and closing body 220 is connected to an upper end of the tube body 210. The sample collection tool 100 may be accommodated in the internal space in the tube body 210.

The top here of the tube body 210 may be sealed with a sealing film (not illustrated), and the sealing film may be removed when molecular diagnostic testing is performed. A stepped jaw 211 may be formed on an outer circumferential surface of the tube body 210, and a concave groove 213 may be formed in the outer circumferential surface thereof. With the stepped jaw 211 and the concave groove 213, the tube body 210 are hooked onto the cartridge 300 for being combined therewith. The stepped jaw 211 is formed to have a diameter relatively greater than a diameter of the tube body 210. When the tube body 210 is seated in the cartridge 300, the stepped jaw 211 is hooked onto an insertion hall 331 in a cartridge holder 330 for combining the tube body 210 with the cartridge 300. Thus, the tube body 210 can be prevented from deviating from the cartridge 300.

The concave groove 213 is formed along the outer circumferential surface of the tube body 210 in such a manner as to have a diameter relatively smaller than the diameter of the tube body 210. The concave groove 213 is formed at a position corresponding to a combination protrusion 335 of the cartridge holder 330. The combination protrusion 335 is hooked onto the concave groove 213 for combining the tube body 210 with the cartridge 300. Accordingly, with an elastic force of an elastic member 333 provided on the combination protrusion 335, the tube body 210 is pressed against the cartridge 300 in a state of being inserted thereinto. Thus, the buffer tube 200 may be fixed together with the cartridge 300.

The tube body 210, as illustrated in FIG. 3B, may include a backward-flowing prevention jaw 215 on the bottom surface. The backward-flowing prevention jaw 215 here may be formed to have the shape of a ring in such a manner as to protrude from the bottom surface of the tube body 210.

The backward-flowing prevention jaw 215 may be formed in such a manner as to have a smaller width than the bottom surface of the tube body 210. As illustrated in FIG. 3C, the backward-flowing prevention jaw 215 may be formed in such a manner as to have a height at which one portion of an inlet port 310 is blocked when the tube body 210 is combined with the cartridge 300. In addition, it is desirable that the backward-flowing prevention jaw 215 is formed in such a manner that an outer diameter thereof is equal to an inner diameter of a support jaw 311a of the tube accommodation body 311.

Accordingly, when the sample solution accommodated within the tube body 210 is discharged, the sample solution flows through the inlet port 310 only to a plurality of fluid channels 315, and a flow of the sample solution between an outer wall of the tube body 210 and an inner wall of the cartridge 300 is limited. Thus, the sample solution can be prevented from flowing backward along an outer lateral surface of the tube body 210. In addition, the sample solution is not brought into contact with the outer lateral surface of the tube body 210. Thus, the sample solution can be prevented from coming into contact with a contamination source that may be present on an outer wall of the tube body 210.

The opening and closing body 220 is combined with the upper end of the tube body 210 and opens and closes the internal space in the tube body 210. The opening and closing body 220, as illustrated in FIG. 4A to 4C, may include a concave-convex pattern 221, a protrusion jaw 223, a through-hole 225, a plurality of vent holes 227, and a hook jaw 229. The concave-convex pattern 221 is formed on an upper surface of the opening and closing body 220. The concave-convex pattern 221 can minimize an area of the opening and closing body 220 with which a user's hand comes into contact during an operation of opening and closing the diagnosis module main body 400 and while the buffer tube 200 is inserted into the cartridge 300. Thus, the sample can be prevented from being contaminated.

The protrusion jaw 223 is formed to have the shape of a ring in such a manner as to protrude from a bottom surface of the opening and closing body 220. An outer circumferential surface of the protrusion jaw 223 is inserted into an inner circumferential surface of the tube body 210. The through-hole 225 is formed in a central area of the opening and closing body 220 in a manner that passes therethrough from the upper surface to the lower surface.

Each of the plurality of vent holes 227 is formed in the lower surface of the opening and closing body 220 between a lateral surface of the through-hole 225 and the protrusion jaw 223. The plurality of vent holes 227 may be formed in such a manner as to be spaced apart a predetermined distance from each other.

The hook jaw 229 extends inward from the lateral surface of the through-hole 225 and thus supports the inlet-port plugging member 230. At this point, when the inlet-port plugging member 230 is moved, a shape of a curved surface of the hook jaw 229 may be changed by a pressing pressure transferred through the inlet-port plugging member 230 and thus may support the inlet-port plugging member 230 in a state where the inlet-port plugging member 230 is no longer moved.

The inlet-port plugging member 230 is inserted into the through-hole 225 in the opening and closing body 220 and seals the internal space in the tube body 210. At this point, the inlet-port plugging member 230 may be supported by the hook jaw 229. The inlet-port plugging member 230, when pressed by the operation of opening and closing the diagnosis module main body 400, is moved toward the internal space in the tube body 210 and thus opens the plurality of vent holes 227. That is, by the operation of opening and closing the diagnosis module main body 400, the inlet-port plugging member 230 forms an air introduction path along which air flows into the internal space.

The inlet-port plugging member 230 may be formed of a material that can allow air to pass through and can block passage of the sample solution (or the buffer solution). That is, the inlet-port plugging member 230 may be formed of a hydrophobic material in such a manner that the sample solution is prevented from flowing to the outside even when the buffer tube 200 or the cartridge 300 is turned upside down. The inlet-port plugging member 230 may be formed to a predetermined length in such a manner as to perform a plugging function.

Figure 5:
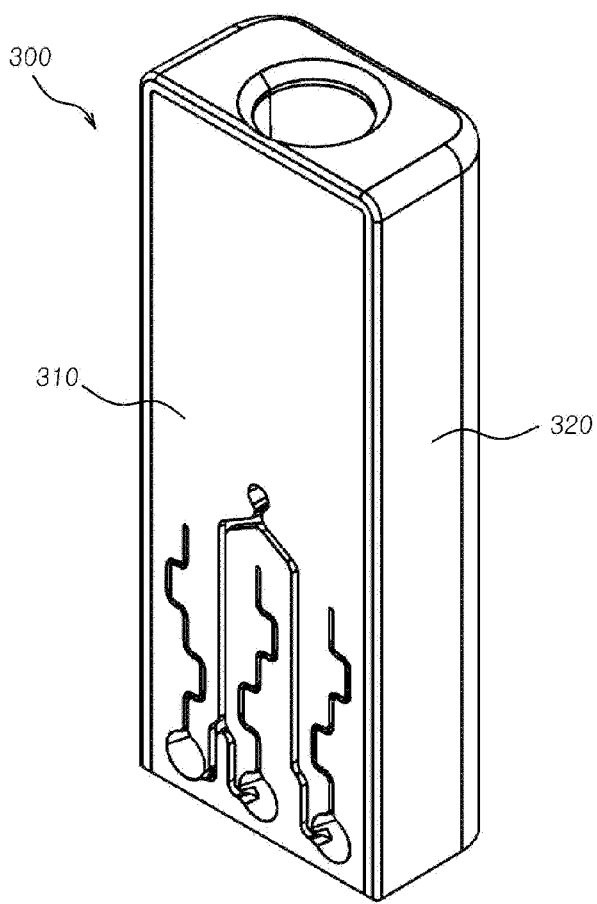
FIG. 5 is a view illustrating a cartridge illustrated in FIG. 1.
Figure 6A:
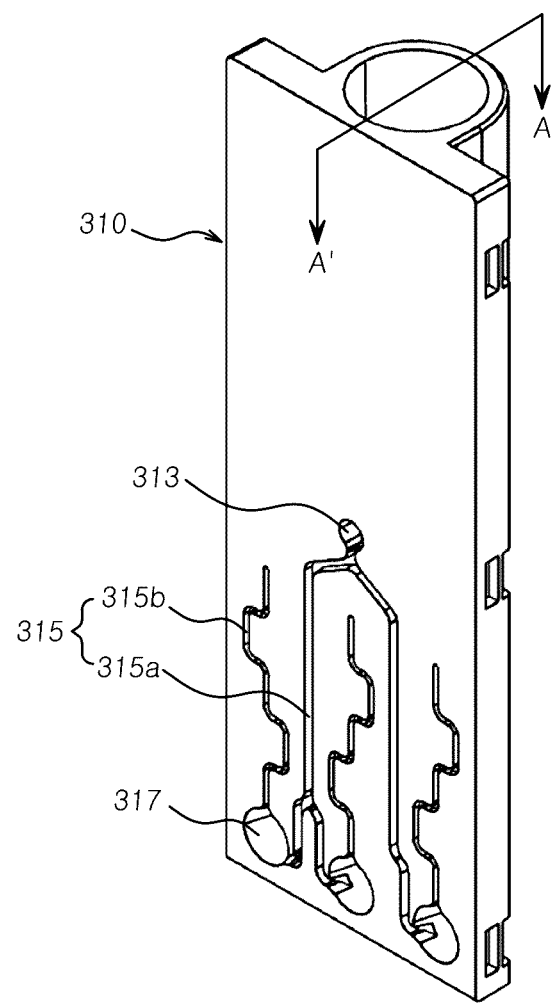
FIGS. 6A to 6D are views each illustrating a cartridge main body illustrated in FIG. 5.
Figure 6B:
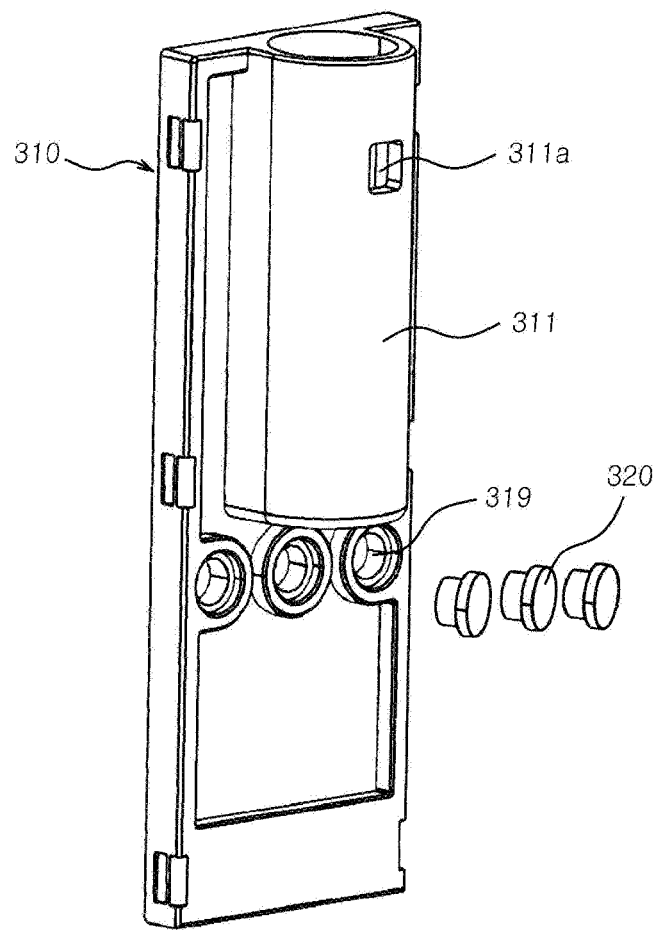
Figure 6C:
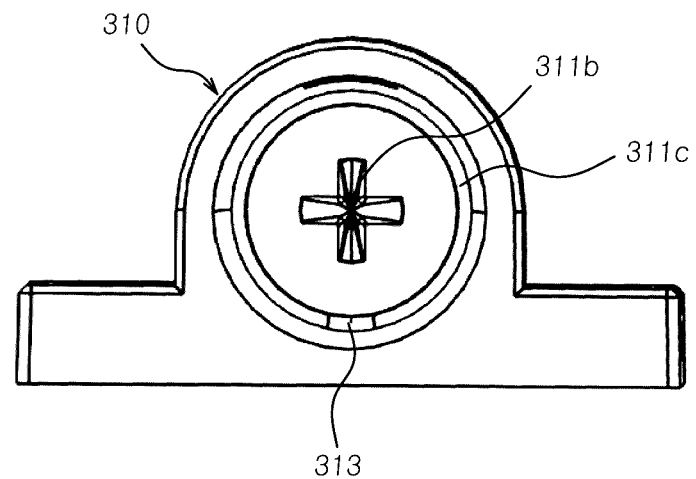
Figure 6D:
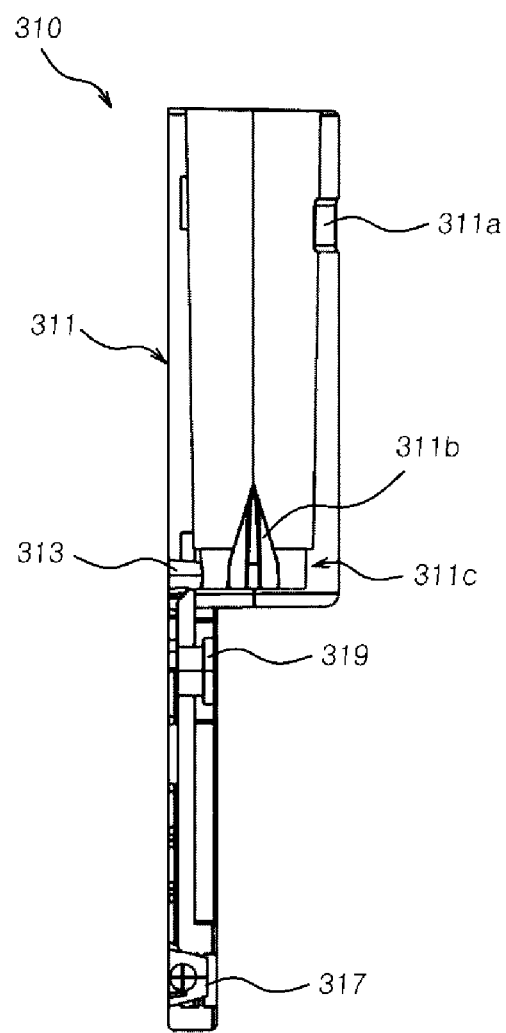
Figure 7A:
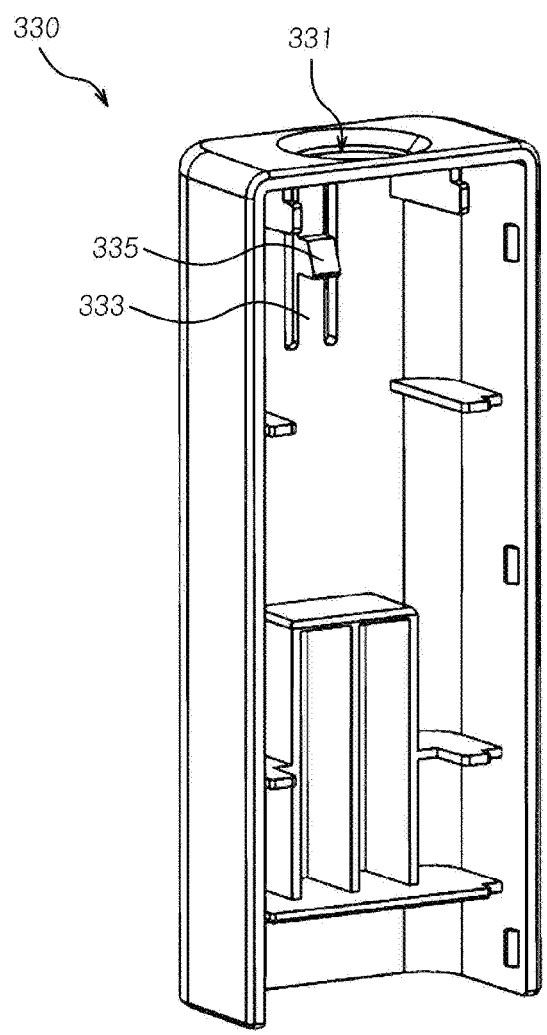
FIGS. 7A and 7B are views each illustrating a cartridge holder illustrated in FIG. 5.
Figure 7B:
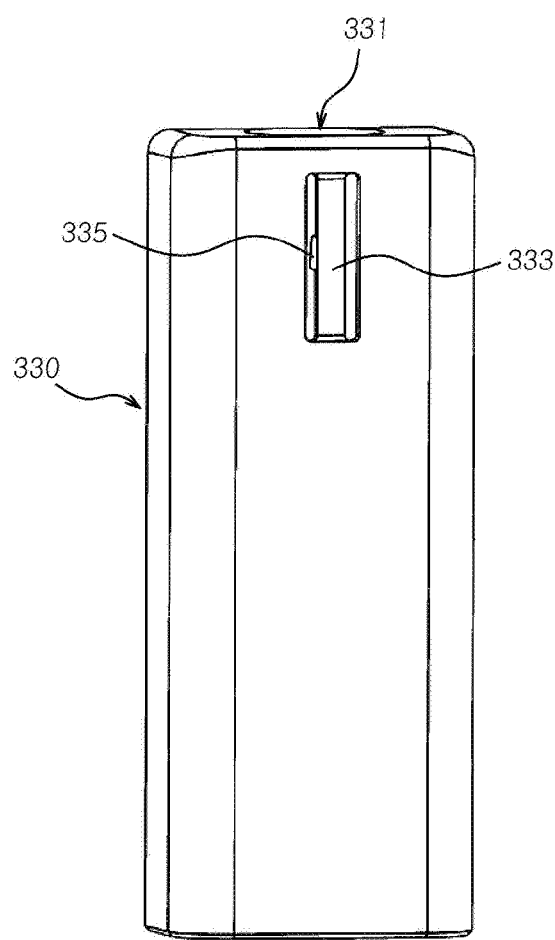

FIG. 5 is a view illustrating an implementation example of the cartridge 300 illustrated in FIG. 1. FIGS. 6A to 6D are views each illustrating a cartridge main body illustrated in FIG. 5. FIGS. 7A and 7B are views each illustrating the cartridge holder 330 illustrated in FIG. 5. FIG. 6C is a top view illustrating a cartridge main body illustrated in FIG. 6A. FIG. 6D is a cross-sectional view taken along line A-A' on FIG. 6A.

With reference to FIG. 5, the cartridge 300 may include a cartridge body 310, a plurality of outlet-port plugging members 320, and the cartridge holder 330. The cartridge body 310 here, as illustrated in FIG. 6A to 6D, is formed in a manner that is based on the shape of a plate with a front surface and a rear surface and may include the tube accommodation body 311, an inlet port 313, the plurality of fluid channels 315, a plurality of reaction chambers 317, and a plurality of outlet ports 319.

The tube accommodation body 311 is formed to have a protruding shape in such a manner as to constitute a front portion of the cartridge body 310. The tube accommodation body 311 is open at the top and has an internal space into which the buffer tube 200 is inserted. The internal space here may be formed to have the same shape and size as the buffer tube 200. Thus, when the tube body 210 is combined with the cartridge 300, the sample solution may be limited to flowing only to the inlet port 310.

The tube accommodation body 311 may include a combination hole 311a, a hole drilling member 311b, and the support jaw 311c. The combination hole 311a here may be formed in a front surface of the tube accommodation body 311 in a manner that passes through the tube accommodation body 311 from a front surface thereof to the inside at a position corresponding to the combination protrusion 335 of the cartridge holder 330

The hole drilling member 311b may be formed on a support surface of the tube accommodation body 311. The hole drilling member 311b drills a hole in a bottom surface of the buffer tube 200 using a pressure applied with an operation of inserting the buffer tube 200. The hole drilling member 311b may be formed in such a manner as to protrude upward from the support surface of the tube accommodation body 311 and to have a pointed end portion.

The support jaw 311c may be formed in such a manner as to protrude toward the internal space along with an inner lateral surface of the tube accommodation body 311 other than the inlet port 313 and may be formed to a predetermined height from the support surface of the tube accommodation body 311. That is, the support jaw 311c may be formed to have the shape of a ring in such a manner as to surround the support surface of the tube accommodation body 311.

The support jaw 311c supports the backward-flowing prevention jaw 215 of the tube body 210, when the tube body 210 is inserted into the internal space in the tube accommodation body 311. That is, the backward-flowing prevention jaw 215 is combined with the support jaw 311c in such a manner that an outer lateral surface thereof is brought into contact with an inner lateral surface of the support jaw 311c. Accordingly, the sample solution is limited to flowing only to the inlet port 313.

The inlet port 313 is formed in a rear surface of the cartridge body 310 in a manner that passes through the cartridge body 310 from a rear surface thereof to the outside on the support surface of the tube accommodation body 311. Through the inlet port 313, the sample solution discharged from the bottom surface of the buffer tube 200 is introduced into each of the plurality of the fluid channels 315.

Each of the plurality of the fluid channels 315 may be formed in the rear surface of the cartridge body 310. Along the plurality of the fluid channels 315, the sample solution may be transported from the inlet port 313 through the corresponding reaction chamber 317 to the corresponding outlet port 319. Each of the plurality of fluid channels 315 here may include a first flow path 315a and a second flow path 315b.

The first flow path 315a may be formed in such a manner as to branch out to each of the plurality of reaction chambers 317 from the inlet port 313. The second flow path 315b may be formed between the corresponding reaction chamber 317 and the outlet port 319. The second flow path 315b may be formed in such a manner as to be curved in a zigzag fashion when viewed from above in order to increase fluid resistance. Accordingly, the flow resistance of the sample solution flowing along the second flow path 315b is increased, and thus a flowing speed can be uniformly maintained.

The plurality of reaction chambers 317 are formed in the rear surface of the cartridge body 310 and accommodate the sample solution transported along the plurality of fluid channels 315, respectively. Each of the plurality of reaction chambers 317 here may include the pre-injected reagent. Each of the plurality of reaction chambers 317 may be supplied with heat at a predetermined temperature from the diagnosis module main body 400 and may perform the nucleic acid amplification reaction on the sample solution. Each of the plurality of reaction chambers 317 may be formed in such a manner as to be of sufficient size to contain a fixed amount of sample solution.

According to the first embodiment of the present disclosure, as an example, the case where three reaction chambers 317 are provided is described above, but the present disclosure is not limited to this case. The number of reaction chambers 317 can be increased or decreased according to the number of diagnosis targets.

Each of the plurality of outlet ports 319 is formed in a front surface of the cartridge body 310 in such a manner as to be positioned between the corresponding reaction chamber 317 and the tube accommodation body 311. That is, each of the plurality of outlet ports 319 is positioned more upward than the corresponding reaction chamber 317. Thus, a state where each of the plurality of reaction chambers 317 is filled with the sample solution can be maintained.

The cartridge body 310 according to the first embodiment of the present disclosure may further include a sealing member (not illustrated) sealing the inlet port 313, the plurality of fluid channels 315, and the plurality of reaction chambers 317 on the rear surface. The sealing member may be formed as a transparent thin film.

The plurality of outlet-port plugging members 320 may be inserted into the plurality of outlet ports 319, respectively. Each of the plurality of outlet-port plugging members 320 can allow air to pass through and can block discharge of the sample solution flowing along each of the plurality of fluid channels 315. Each of outlet-port plugging members 320 may be formed of a porous material, for example, porous polyethylene or porous hydrogel. Therefore, the fluid channel 315 can be kept stationary within the plurality of fluid channels without being discharged to the outside.

The cartridge holder 330 is combined with the front surface of the cartridge body 310 and thus holds the buffer tube 200 in place within the cartridge body 310. The cartridge holder 330, as illustrated in FIGS. 7A and 7B, may have the internal space into which the cartridge body 310 is inserted and may include the insertions hole 331, the elastic member 333, and the combination protrusion 335.

The insertion hole 331 is formed at a position corresponding to an upper end portion of the tube accommodation body 311. Through the insertion hole 331, the internal space of the tube accommodation body 311 is exposed. The elastic member 333 has the shape of a plate spring and is positioned on an inner lateral surface of the cartridge holder 330 that faces the tube accommodation body 311. With a sliding motion due to the insertion of the buffer tube 200, the elastic member 333 is elastically deformed and thus provides an elastic force to the combination protrusion 335.

The combination protrusion 335 is formed in such a manner as to protrude from the elastic member 333 at a position corresponding to the combination hole 311a in the tube accommodation body 311 and is inserted into the combination hole 311a. The combination protrusion 335 has an inclined surface and causes the elastic member 333 to be maximally elastically deformed at an end of the inclined surface. Thus, a restoring force that acts when the elastic member 333 is restored to its original position can be increased. With the sliding motion due to the insertion of the buffer tube 200, the combination protrusion 335 reaches the concave groove 213. At this time, the combination protrusion 335 is supplied with the elastic force from the elastic member 333. Thus, the combination protrusion 335 is hooked onto the concave groove 213 for being fastened thereto, making a slight sharp "click" sound.

That is, when hooked onto the concave groove 213 for being combined therewith, the combination protrusion 335 makes a slight sharp "click" sound. Thus, it can be ensured that the tube body 210 is completely combined with the cartridge body 310 in such a manner as to be positioned at its home position. Once the combination protrusion 335 combines the buffer tube 200 and the cartridge body 310 into one piece, the buffer tube 200 is not allowed to be separated from the cartridge body 310.

Figure 8:
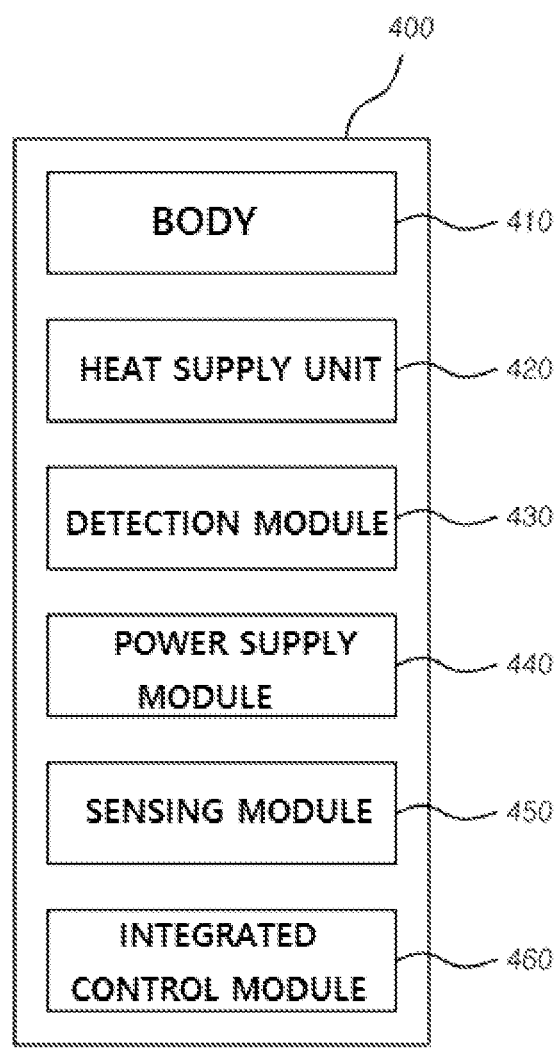
FIG. 8 is a block diagram illustrating a diagnosis module main body illustrated in FIG. 1.
Figure 9:
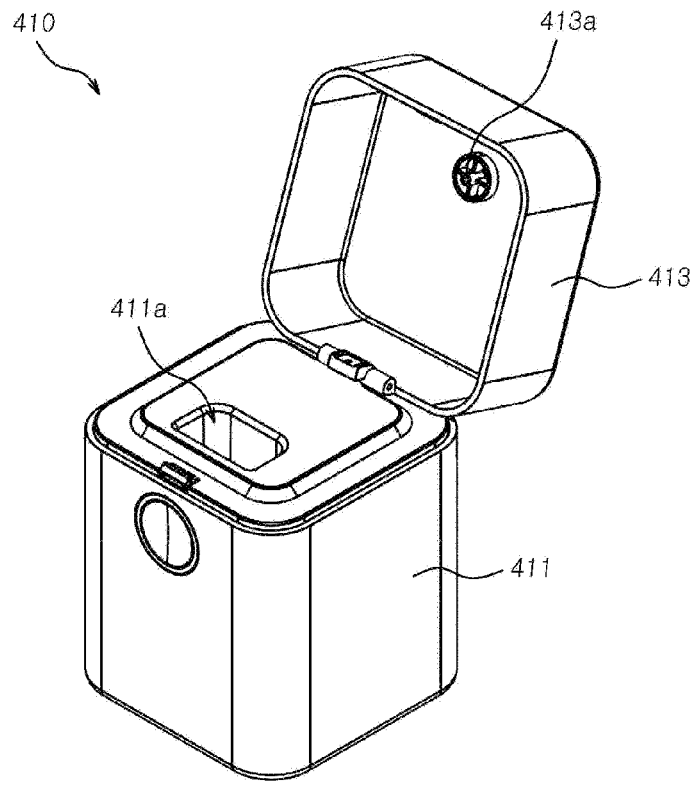
FIG. 9 is a view illustrating a body of the diagnosis module main body illustrated in FIG. 8.
Figure 10:
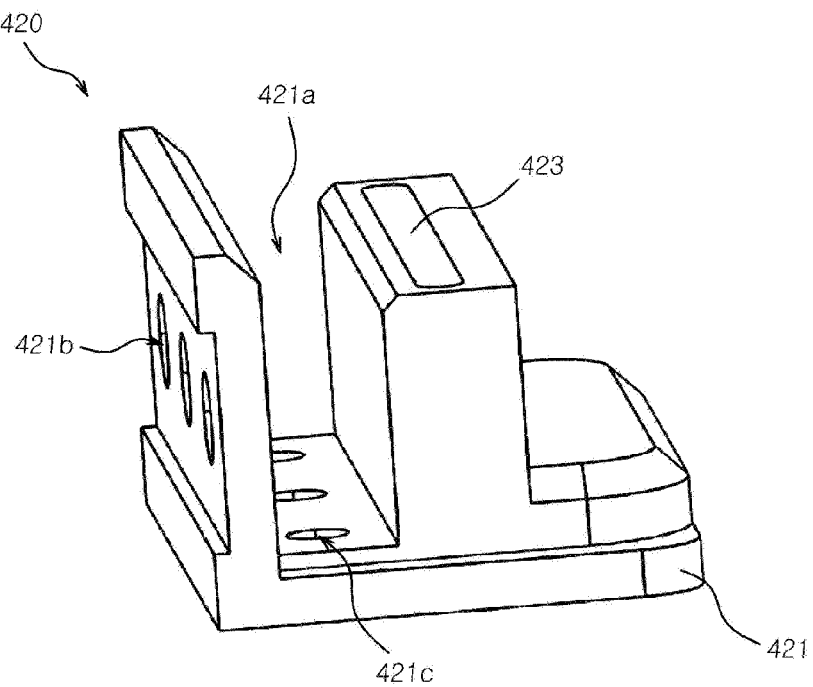
FIG. 10 is a view illustrating a heat supply module illustrated in FIG. 8.
Figure 11:
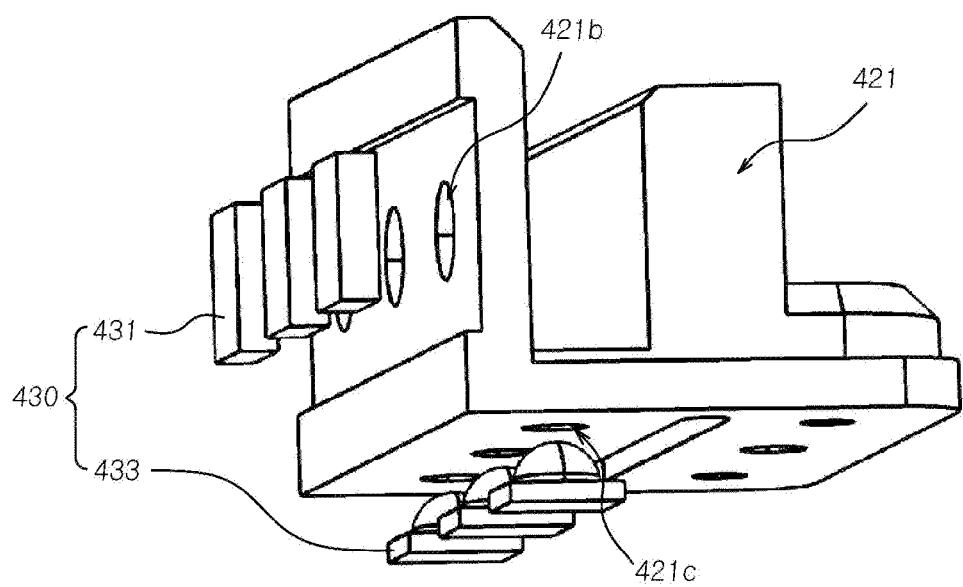
FIG. 11 is a view illustrating a detection module illustrated in FIG. 8.

FIG. 8 is a block diagram illustrating the diagnosis module main body 400 illustrated in FIG. 1. FIG. 9 is a view illustrating a body illustrated in FIG. 8. FIG. 10 is a view illustrating a heat supply module illustrated in FIG. 8. FIG. 11 is a view illustrating a detection module illustrated in FIG. 8.

With reference to FIG. 8, the diagnosis module main body 400 may include a body 410, a heat supply module 420, a detection module 430, a power supply module 440, a sensing module 450, and an integrated control module 460. The body 410 accommodates the cartridge 300, the heat supply module 420, the detection module 430, the power supply module 440, and the integrated control module 460. The body 410, as illustrated in FIG. 9, may include the lower body 411 and the opening and closing body 413. The lower body 411 may be formed to have the shape of a rectangle and has an internal space of predetermined size. The lower body 411 may include an insertion hole 411a. The insertion hole 411a may be formed in an upper surface of the lower body 411. The insertion hole 411a may be formed to have a shape and size corresponding to the cartridge 300 so that the cartridge 300 can be inserted into the insertion hole 411a.

The opening and closing body 413 is combined with the lower body 411 and opens and closes the internal space in the lower body 411. The opening and closing body 413 may include a pressing member 413a. The pressing member 413a may be formed in such a manner as to protrude from an inner surface corresponding to the upper surface of the lower body 411 and may be formed at a position corresponding to the inlet-port plugging member 230 of the buffer tube 200. The pressing member 413a may press the inlet-port plugging member 230 for movement thereof.

The heat supply module 420 is detachably combined with the cartridge 300. Under the control of the integrated control module 460, the heat supply module 420 supplies heat at a predetermined temperature, which is necessary for the nucleic acid amplification reaction, to each of the plurality of reaction chambers 317.

The heat supply module 420, as illustrated in FIG. 10, may include a thermal conductivity body 421 and a heating unit 423. The thermal conductivity body 421 is combined with the cartridge 300. The thermal conductivity body 421 is supplied with heat at a temperature from the heating unit 423 and transfers the heat to the cartridge 300. The thermal conductivity body 421 accommodates the cartridge 300 and the heating unit 423 and may include a cartridge insertion groove 421a, a plurality of first holes 421b, and a plurality of second holes 421c.

The cartridge insertion groove 421a may be formed at a position corresponding to the insertion hole 411a in the lower body 411. The cartridge insertion groove 421a may be formed in such a manner that an inner surface thereof is brought into contact with a front surface, a rear surface, and a bottom surface of a portion of the cartridge 300, the portion including the plurality of reaction chambers 317.

Each of the plurality of first holes 421b is formed in the cartridge insertion groove 421a in a manner that passes therethrough from the one-side inner surface to the outside. The plurality of first holes 421b may be formed at positions, respectively, that correspond to the plurality of reaction chambers 317.

Each of the plurality of second holes 421c is formed in the cartridge insertion groove 421a in a manner that passes through a bottom surface thereof. The plurality of second holes 421c may be formed at positions, respectively, that correspond to the plurality of reaction chambers 317.

The heating unit 423 is arranged within the thermal conductivity body 421 and generates heat at a predetermined temperature. Examples of the heating unit 423 may include a resistive heater, a thermoelectric element, and the like.

The first embodiment of the present disclosure is not limited to this heating unit 423. The heat supply module 420 may further include a heat sink or the like that dissipates heat of the thermal conductivity body 421 to the outside.

The detection module 430 is arranged adjacent to the heat supply module 420. Under the control of the integrated control module 460, the detection module 430 emits light to each of the plurality of reaction chambers 317, detects light that passes through each of the plurality of reaction chambers 317, and generates a detection signal.

The detection module 430, as illustrated in FIG. 11, may include a plurality of light sources 431 and a plurality of light detectors 433. Under the control of the integrated control module 460, the plurality of light sources 431 may emit light to the plurality of reaction chambers 317, respectively. Each of the plurality of light sources 431 may be formed as a light emitting diode (LED) or a laser diode (LD).

The plurality of light sources 431 here may be arranged adjacent to the plurality of second holes 421c, respectively, in the thermal conductivity body 421. The plurality of light sources 431 may be arranged in a direction horizontal or vertical to the light detectors 433, respectively, with reference to the cartridge 300. According to the first embodiment of the present disclosure, as an example, the case where the plurality of light sources 431 are arranged in the direction vertical to the plurality of light detectors 433, respectively, but the first embodiment of the present disclosure is not limited to this case. The plurality of light sources 431 may be arranged in the direction horizontal to the plurality of light detectors 433, respectively, with reference to the cartridge 300.

It is desirable that the light source 431 may be arranged in the direction horizontal to the light detector 433 in a case where the light detector 433 detects color of the sample solution. Furthermore, it is desirable that the light source 431 may be arranged in the direction vertical to the light detector 433 in a case where the light detector 433 detects fluorescent of the sample solution.

The plurality of light detectors 433 may detect light that passes through the plurality of reaction chambers 317, respectively. Then, the light detectors 433 may generate the detection signal and may transmit the generated detection signal to the integrated control module 460. The plurality of light detectors 433 may be arranged in such a manner as to face the plurality of reaction chambers 317, respectively. The plurality of light detectors 433 may be arranged adjacent to the plurality of first holes 421b, respectively, in the thermal conductivity body 421. Each of the plurality of light detectors 433 here may include a photodiode (PD), a photo multiplier tube (PMT), a phototransistor, a charge-coupled device (CCD) image sensor, or a complementary metal-oxide semiconductor (CMOS) image sensor.

The power supply module 440 may supply electric power to each of the heat supply module 420, the detection module 430, and the integrated control module 460. The power supply module 440 may include a battery, a power button, a power terminal, and the like.

The sensing module 450 may sense a closed state of the body 410 and may generate an opening and closing sensing signal. Furthermore, the sensing module 450 may sense temperature of the heat supply module 420 and may generate a temperature sensing signal. The sensing module 450 may include a plate spring member (not illustrated) supporting the opening and closing body 413, a pressure sensor (not illustrated), and a temperature sensor (not illustrated).

Through the pressure sensor, the sensing module 450 may sense an elastic force that is generated from the plate spring member when the opening and closing body 413 is closed, and may generate an opening and closing sensing signal. In addition, through the temperature sensor, the sensing module 450 may sense the temperature of the heat supply module 420 and may generate a temperature sensing signal.

According to the detection signal and the opening and closing sensing signal that are transmitted from the detection module 430, the integrated control module 460 may determine whether or not the preset operating condition is satisfied. Specifically, according to the detection signal, the integrated control module 460 may determine whether or not the cartridge 300 is inserted or whether or not the sample solution is transported into the plurality of reaction chambers 317. That is, the integrated control module 460 according to the first embodiment of the present disclosure may determine the operating condition by utilizing the detection module 430 as the sensor for determining whether or not the cartridge 300 is inserted into the body 410 and the sensor for determining whether or not the sample solution is injected into each of the reaction chambers 317.

In addition, according to the opening and closing sensing signal, the integrated control module 460 may determine whether the body 410 is opened or closed. That is, in a case where the cartridge 300 is inserted, where the sample solution is transported into the plurality of reaction chambers 317, and where the body 410 is in a closed state, the integrated control module 460 may determine that all operating conditions are satisfied.

When the operating condition is satisfied, the integrated control module 460 supplies heat at a predetermined temperature, which is necessary for the nucleic acid amplification reaction, to each of the plurality of reaction chambers 317 through the heat supply module 420. According to the temperature sensing signal, the integrated control module 460 may control the temperature of the heat supply module 420 in a manner that is uniformly maintained.

When heat at a predetermined temperature is supplied to each of the plurality of reaction chambers 317, the integrated control module 460 may detect a change in color or in a fluorescent magnitude due to the nucleic acid amplification reaction from the sample solution in each of the plurality of reaction chambers 317 and may determine whether or not the diagnosis target is present. The integrated control module 460 may communicate with the user terminal 2 to transmit the result of diagnosing the diagnosis target. The integrated control module 460 may be controlled by the user terminal 2 and may be realized as a printed circuit board (PCB).

Figure 12:
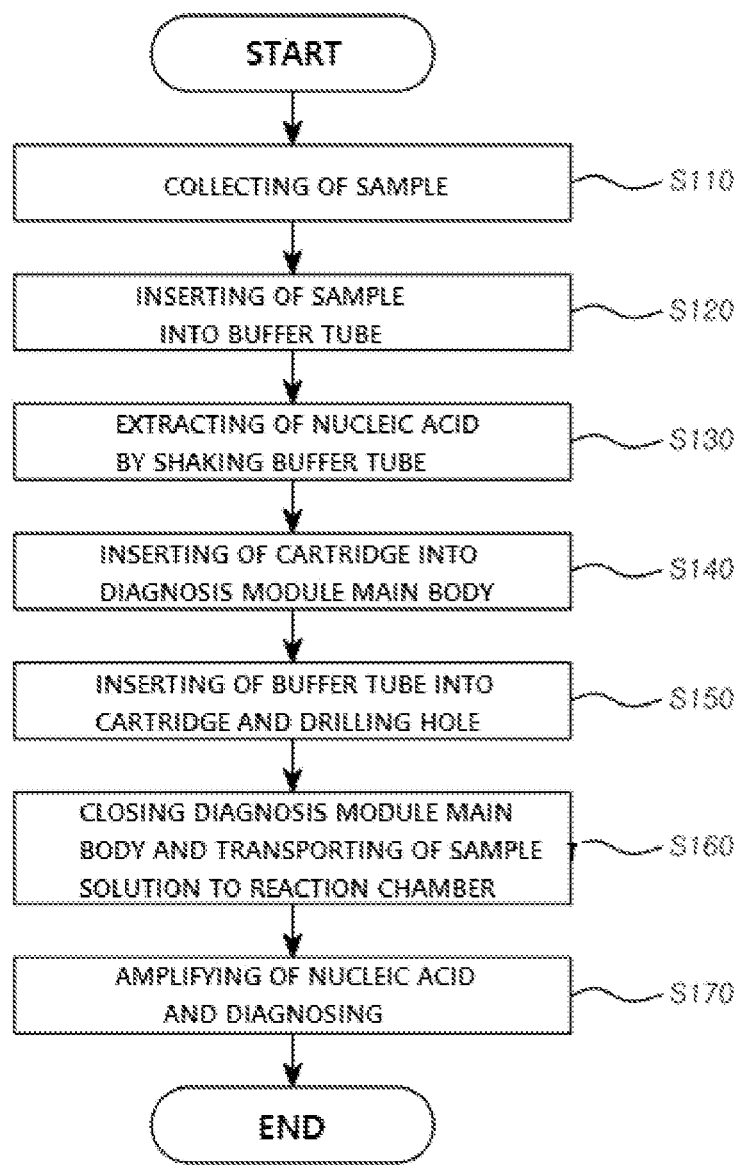
FIG. 12 is a flowchart for a molecular diagnostic method according to a second embodiment of the present disclosure.
Figure 13:
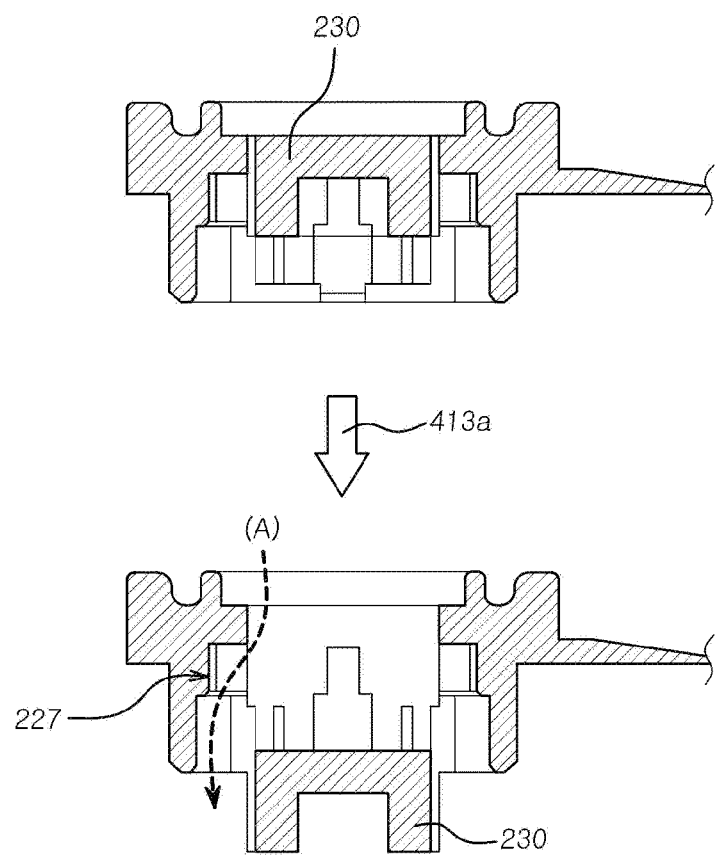
FIG. 13 is a view illustrating a movement of an inlet-port plugging member of a buffer tube.
Figure 14:
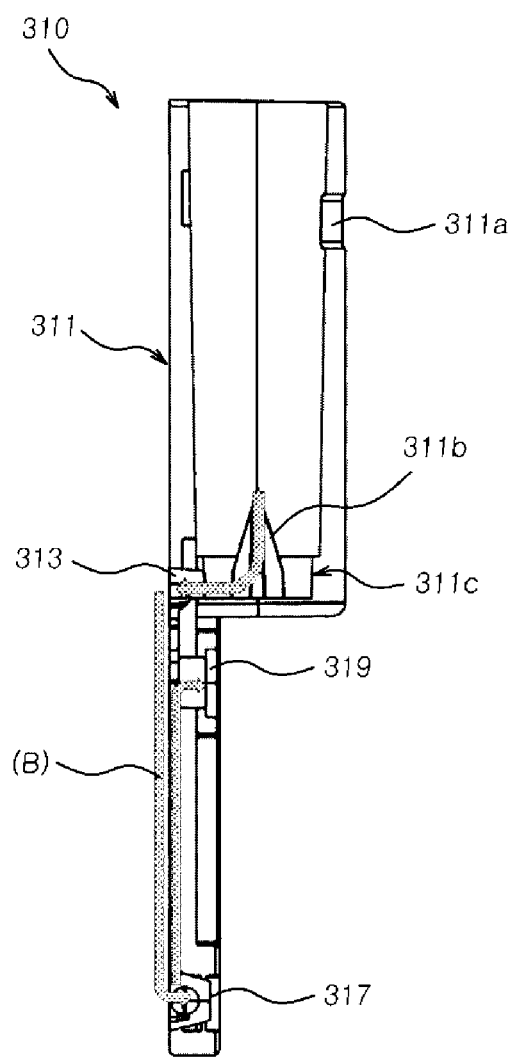
FIG. 14 is a view illustrating a path along which a sample solution flows.
Figure 15A:
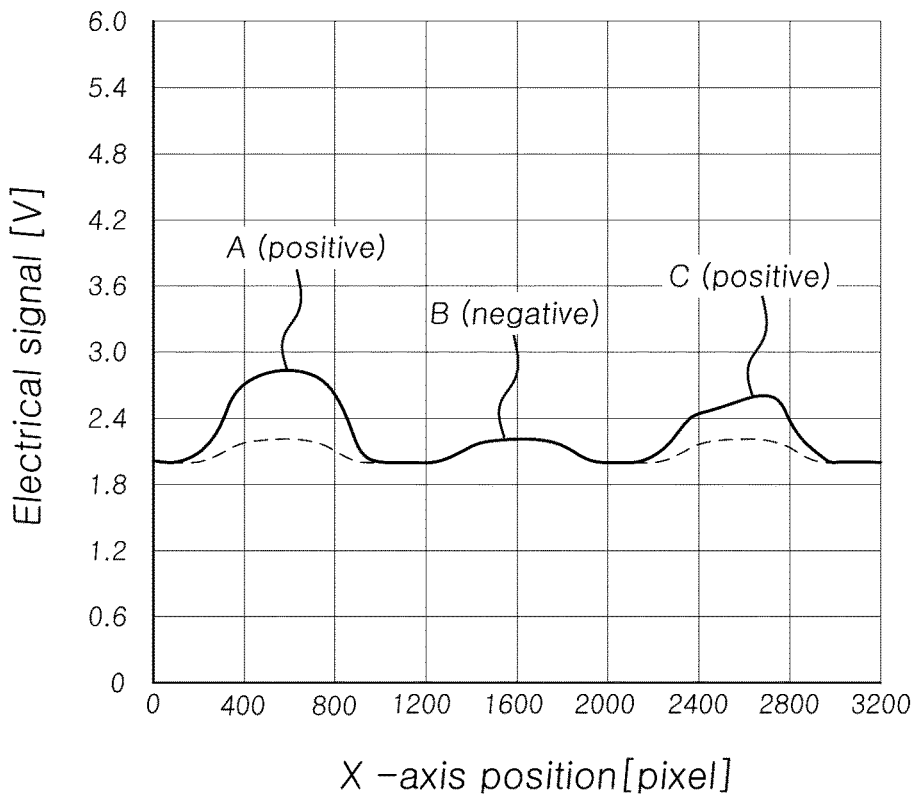
FIGS. 15A and 15B are graphs each illustrating a result of diagnosis.
Figure 15B:
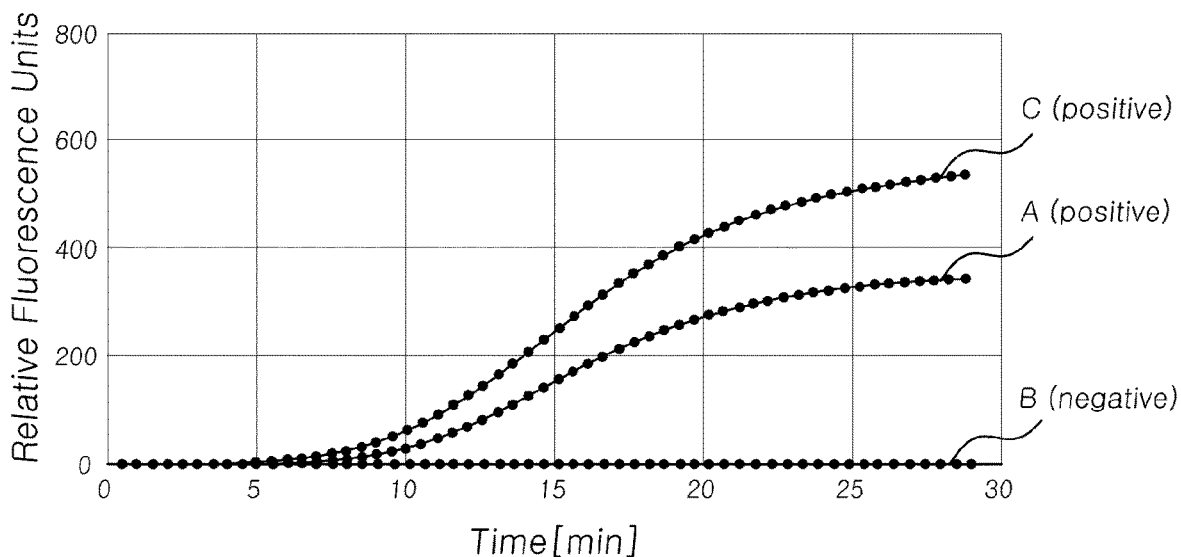

FIG. 12 is a flowchart for a molecular diagnostic method according to a second embodiment of the present disclosure. FIG. 13 is a view illustrating a movement of the inlet-port plugging member 230 of the buffer tube 200. FIG. 14 is a view illustrating a path along which the sample solution flows. FIGS. 15A and 15B are graphs each illustrating the result of the diagnosis.

With reference to FIG. 12, a sample is collected from a user using the sample collection tool 100 (Step S110). Subsequently, the sample collection tool 100 is placed into the tube body 210 of the buffer tube 200 (Step S120). At this time, the sample collection tool 100 is immersed in the buffer solution pre-injected into the buffer tube 200. Subsequently, the opening and closing body 220 is closed. At this time, the inlet-port plugging member 230 is in a state of being fittingly inserted into the through-hole 225 in the opening and closing body 220. Therefore, when the opening and closing body 220 is closed, the tube body 210 is sealed.

Subsequently, the buffer tube 200 is shaken. Then, a cell membrane of the sample collected through the sample collection tool 100 is destroyed, and thus nucleic acid is extracted (Step S130). Accordingly, a sample solution that is obtained by mixing the buffer solution with the nucleic acid is prepared.

In this state, the cartridge 300 is mounted in the diagnosis module main body 400 through the insertion hole 411a in the lower body 411 (Step S140). Then, the buffer tube 200 is inserted into the tube accommodation body 311 of the cartridge 300. At this time, the hole driving member 311b drills a hole in the bottom surface of the tube body 210 (Step S150). Then, the sample solution is discharged from the tube body 210. At this time, the plurality of vent holes 227 are in a state of being closed by the inlet-port plugging member 230 of the buffer tube 200. Therefore, the sample solution is not introduced into the inlet port 313.

In this state, when the opening and closing body 413 is closed, as illustrated in FIG. 13, the pressing member 413a of the opening and closing body 413 presses the inlet-port plugging member 230 of the buffer tube 200, and the inlet-port plugging member 230 is moved downward. Thus, the plurality of vent holes 227 are opened. Accordingly, an air introduction path A along which air is introduced into the internal space in the tube body 210 is formed.

Then, as illustrated in FIG. 14, air flows at both ends of each of the plurality of fluid channels 315. In this state, due to a capillary force, the sample solution flows along a path B from the inlet port 313 through the corresponding reaction chamber 317 to the corresponding the outlet port 319. At this time, each of the plurality of outlet ports 319 is in a state of being closed by the corresponding outlet-port stopper member 320. The sample solution is accommodated in a stationary state within the reaction chamber 317. In this manner, the sample solution is transported into the corresponding reaction chamber 317 along each of the plurality of fluid channels 315 (Step S160).

At this time, according to the detection signal and the opening and closing sensing signal, the integrated control module 460 determines whether or not the operation condition is satisfied. For example, according to the detection signal, the integrated control module 460 may determine whether or not the cartridge 300 is inserted into the body 410 and may determine whether or not the sample solution is injected into each of the reaction chambers 317. Then, according to the opening and closing sensing signal, the integrated control module 460 may determine whether the body 410 is opened or closed. At this point, when the cartridge 300 is inserted into the diagnosis module main body 400 and when the sample solution is injected into each of the reaction chambers 317 in a state where the body 410 is closed, the integrated control module 460 may determine that all the operating conditions are satisfied.

When all the operating conditions are satisfied in this manner, the integrated control module 460 supplies heat at a predetermined heat to the plurality of reaction chambers 317 through the heat supply module 420. Accordingly, the nucleic acid amplification reaction is performed on the sample solution accommodated in each of the plurality of reaction chambers 317. At this time, the detection module 430 detects color or a fluorescent magnitude of the sample solution, generates the detection signal, and transmits the generated detection signal to the integrated control module 460.

Subsequently, according to the detection signal, the integrated control module 460 detects a change in color or in a fluorescent magnitude due to the nucleic acid amplification reaction from the sample solution in each of the plurality of reaction chambers 317 and finds out whether or not the diagnosis target is present.

For example, in a case where there are three reaction chambers 317, that is, reaction chambers A, B, and C, reagents for detecting first type and second type genes for diagnosing COVID-19 may be contained in the reaction chamber A and the reaction chamber B, respectively. An internal control (IC) reagent for checking whether or not the apparatus operates properly and whether or not sample collection is sufficient may be contained in the reaction chamber C. The internal control (IC) regent here is a material for identifying RNA of epithelial tissue. In a case where the sample collection is insufficient, or in a case where the apparatus does not operate properly, a negative response appears.

In this state, when a change in color due to a change in pH before or after the nucleic acid amplification reaction occurs in the sample solution accommodated in each of the reaction chambers A, B, and C, the integrated control module 460 may determine that the diagnosis target is present. To this end, a phenol red indicator or a purple indicator of which color is changed due to the nucleic acid amplification reaction may be contained in the sample solution accommodated in each of the reaction chambers A, B, and C.

For example, as illustrated in FIG. 15A, in a case where color of the sample solution accommodated in each of the reaction chamber A and the reaction chamber B is changed after the nucleic acid amplification reaction, but where color of the sample solution accommodated in the reaction chamber B is not changed, the detection signal corresponding to the change in color in each of the reaction chambers A and C, that is, an electrical output (electrical signal) value is increased in a manner that is higher than an electrical output value (indicated by a dotted line) that is obtained before the nucleic acid amplification reaction. Then, the integrated control module 460 may verify that the sample is appropriately collected and that the apparatus operates and may determine that first type COVID-19 virus is present (a positive response).

Alternatively, the integrated control module 460 may detect the fluorescent magnitude of the sample solution through the nucleic acid amplification reaction and may determine whether or not the diagnosis target is present. For example, as illustrated in FIG. 15B, in a case where, unlike in the reaction chamber B, the fluorescent magnitude of the sample solution accommodated in each of the reaction chamber A and the reaction chamber C is increased, the integrated control module 460 may verify that the sample is appropriately collected and that the apparatus operates properly and may determine that the first type COVID-19 virus is present (a positive response).

Next, the integrated control module 460 provides the result of diagnosing the diagnosis target to the user terminal 2 (Step S170). Subsequently, the buffer tube 200 and the cartridge 300 may be disposed of in a sealed state.

The second embodiment of the present disclosure is not limited to Step S140. In Step S140, when the cartridge 300 is inserted into the diagnosis module main body 400, the cartridge 300 may be inserted into the diagnosis module main body 400 in a state where the buffer tube 200 is inserted into the cartridge 300. That is, the buffer tube 200 may be first inserted into the cartridge 300, and then the cartridge 300 may be inserted into the diagnosis module main body 400, together with the buffer tube 200.

Figure 16:
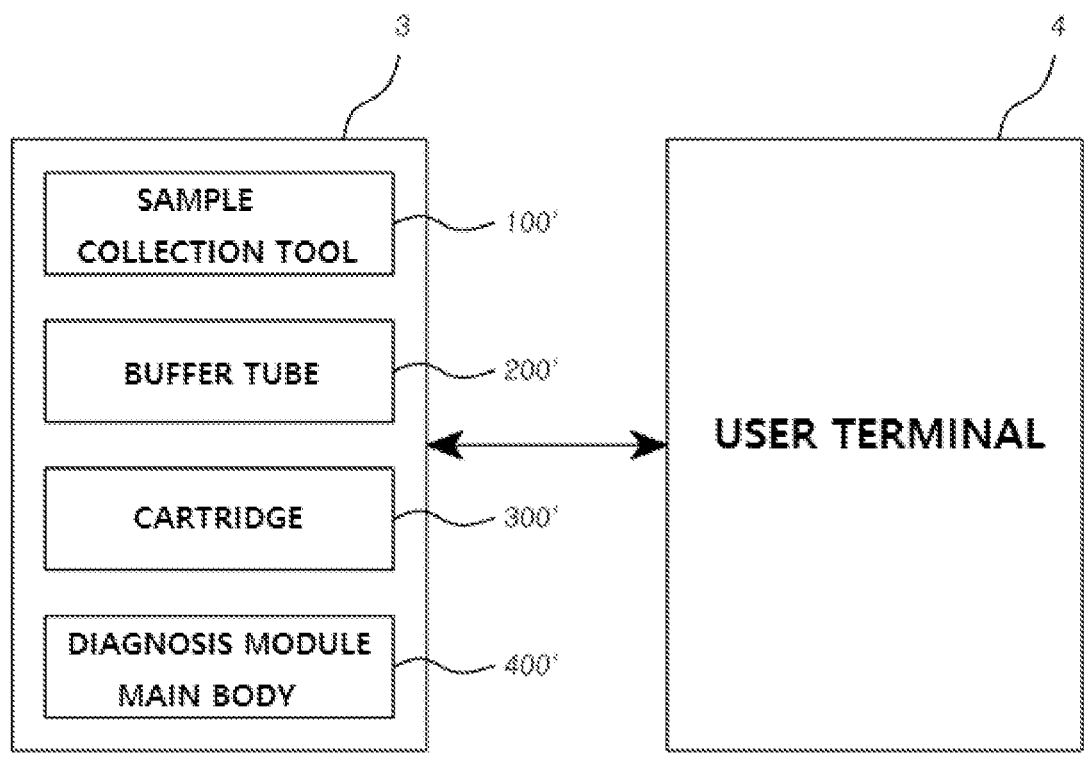
FIG. 16 is a block diagram illustrating an integrated molecular diagnosis system according to a third embodiment of the present disclosure.
Figure 17A:
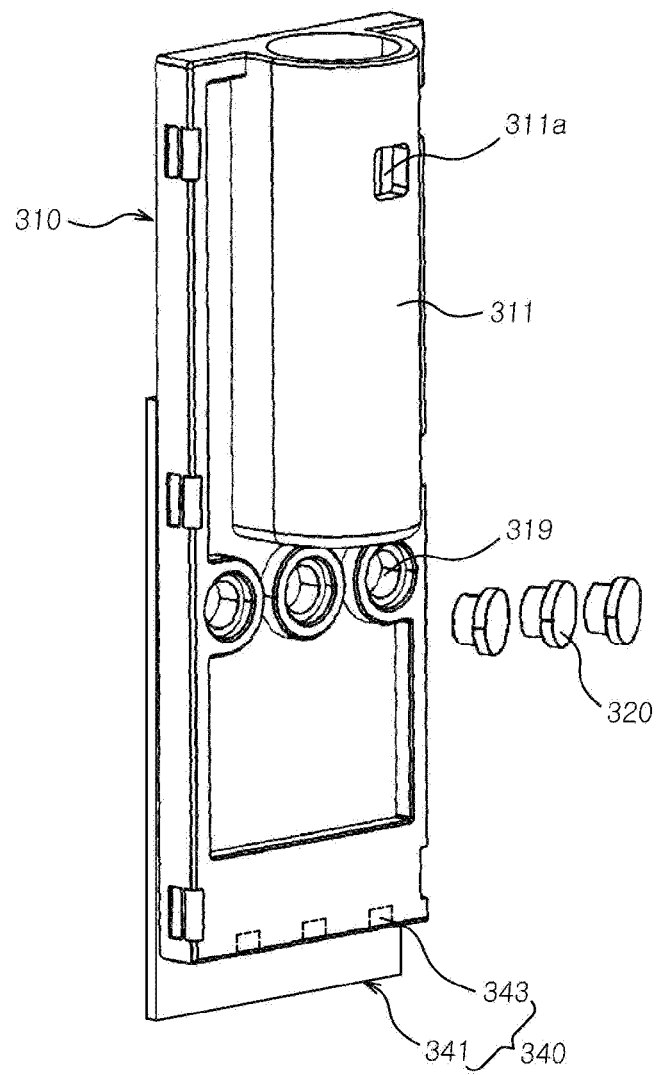
FIGS. 17A to 17C are views each illustrating a cartridge illustrated in FIG. 16.
Figure 17B:
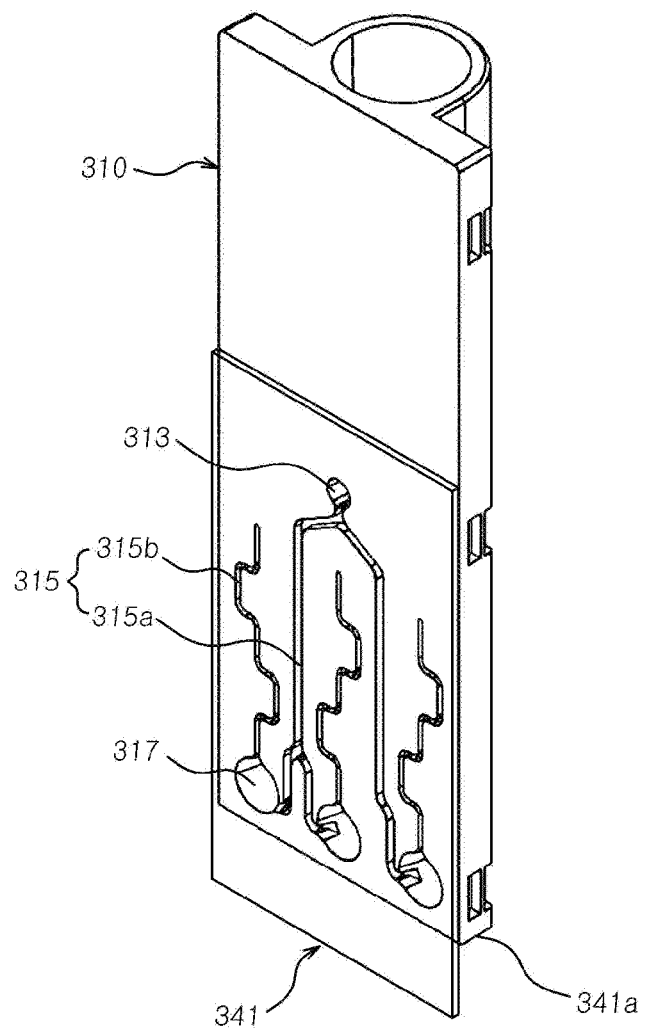
Figure 17C:
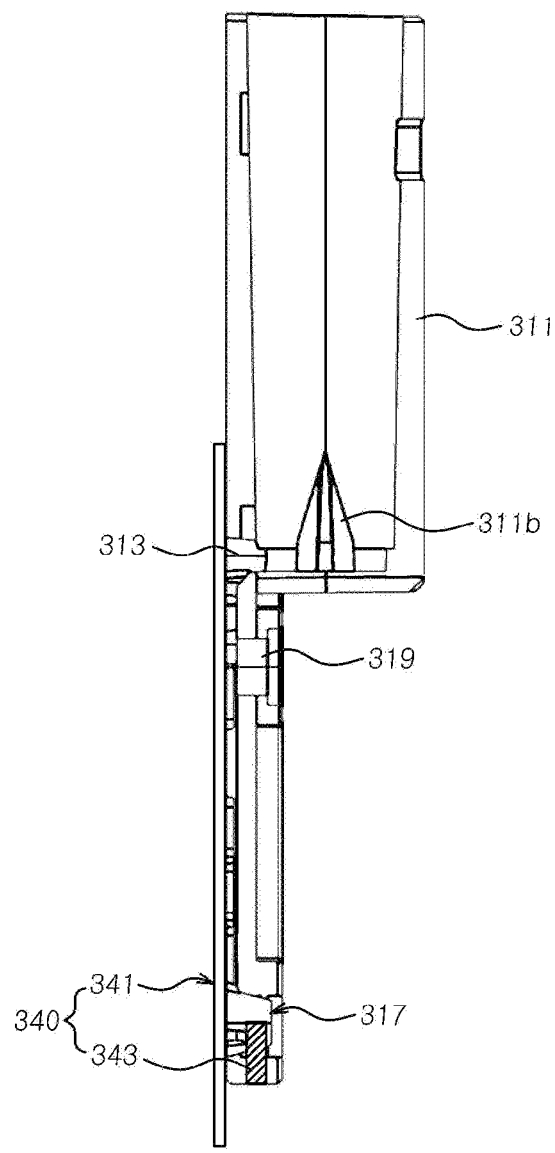
Figure 18:
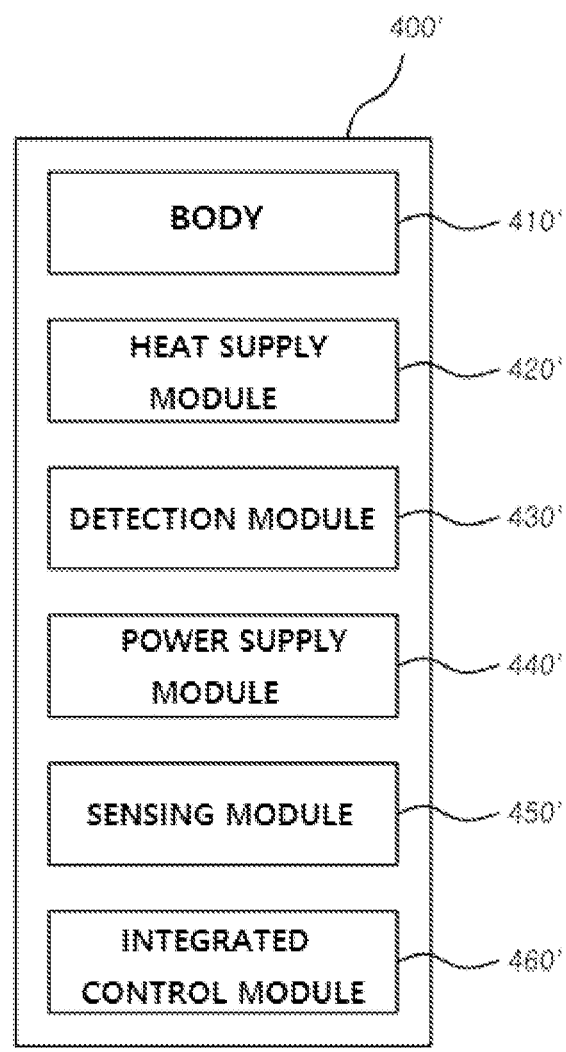
FIG. 18 is a block diagram illustrating a diagnostic module main body illustrated in FIG. 16.
Figure 19:
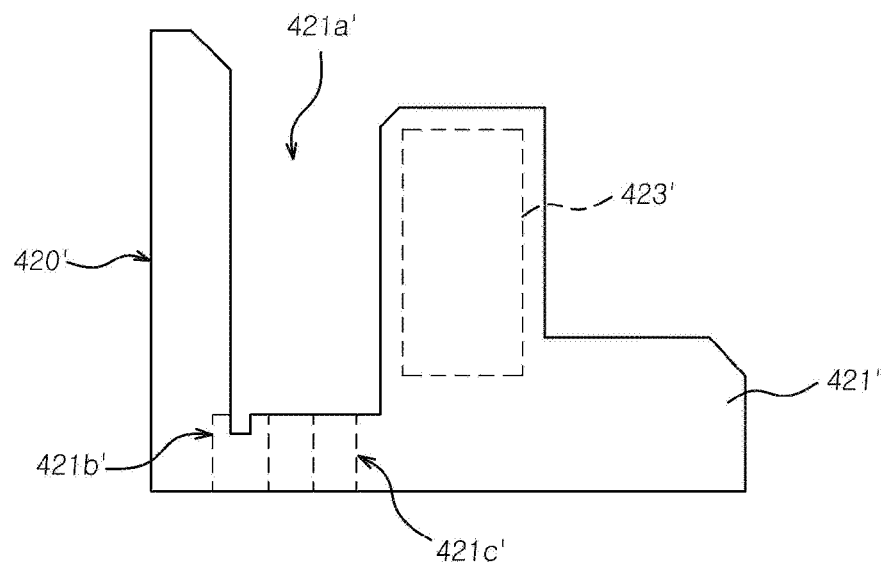
FIG. 19 is a view illustrating a heat supply module illustrated in FIG. 18.
Figure 20A:
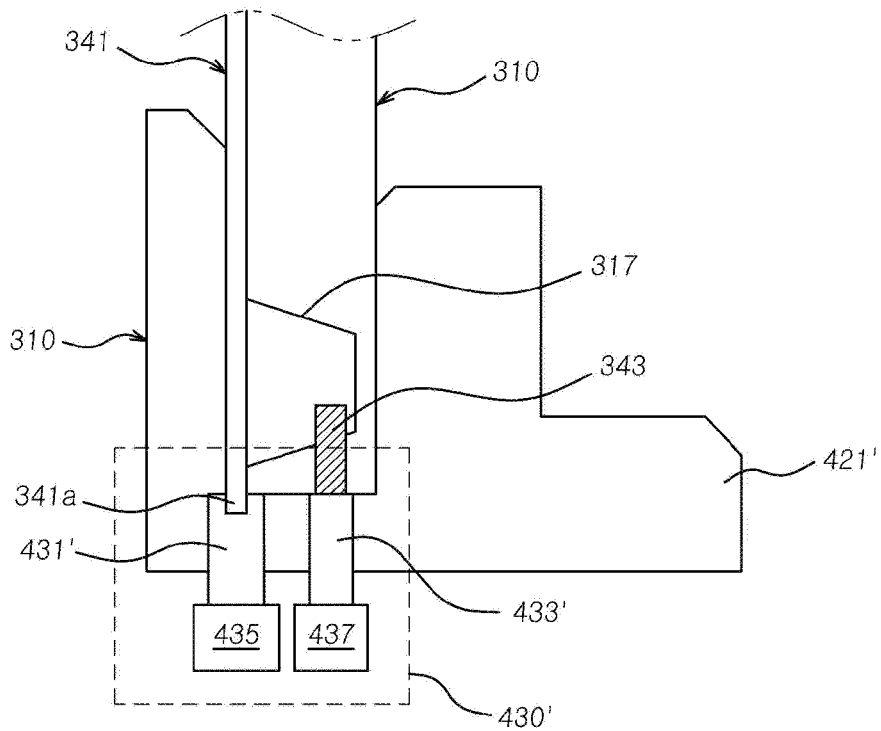
FIGS. 20A and 20B are views each illustrating a detection module illustrated in FIG. 18.
Figure 20B:
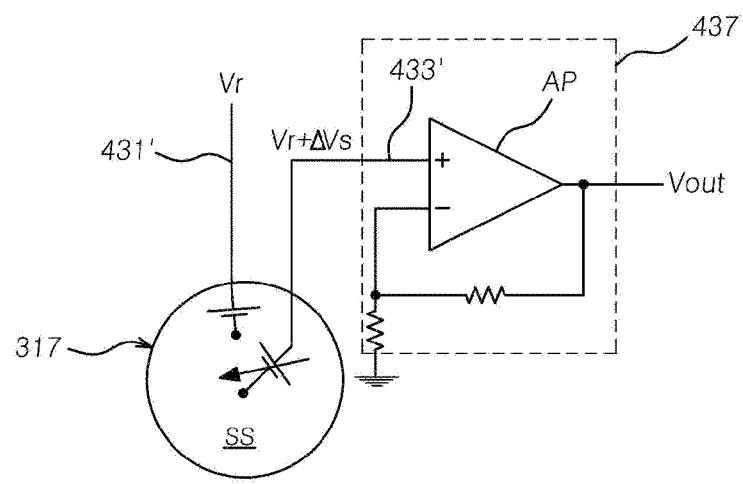
Figure 21:
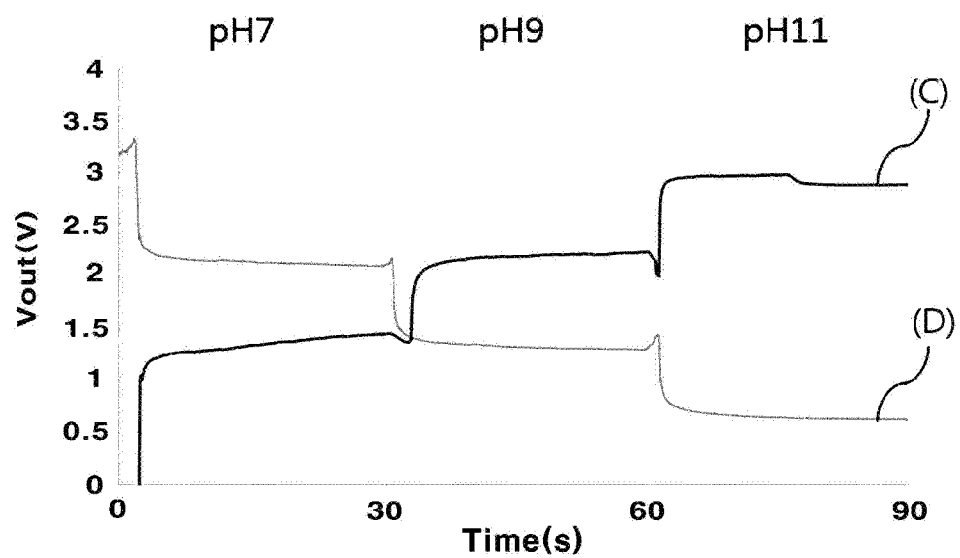
FIG. 21 is a view illustrating a detection signal that is output from the detection module illustrated in FIG. 18.

FIG. 16 is a block diagram illustrating an integrated molecular diagnosis system according to a third embodiment of the present disclosure. FIGS. 17A to 17C are views each illustrating a cartridge illustrated in FIG. 16. FIG. 18 is a block diagram illustrating a diagnostic module main body illustrated in FIG. 16. FIG. 19 is a view illustrating a heat supply module illustrated in FIG. 18. FIGS. 20A and 20B are views each illustrating a detection module illustrated in FIG. 18. FIG. 21 is a view illustrating a detection signal that is output from the detection module illustrated in FIG. 18.

With reference to FIG. 16, an integrated molecular diagnosis system according to a third embodiment of the present disclosure may include an integrated molecular diagnosis apparatus 3 and a user terminal 4. The integrated molecular diagnosis apparatus 3 may include a sample collection tool 100', a buffer tube 200', a cartridge 300', and a diagnosis module main body 400'. In this case, the sample collection tool 100' and the buffer tube 200' have the same configurations as the sample collection tool 100 and the buffer tube 200, respectively, and therefore descriptions thereof are omitted.

The cartridge 300' is the same as the cartridge 300 according to the first embodiment, except that the cartridge 300' further includes a sensing unit 340. Accordingly, the same constituent elements are given the same reference numeral, and descriptions of the same constituent elements are not repeated for convenience of description. The sensing unit 340 here reacts with hydrogen ions contained in the sample solution in each of the plurality of reaction chambers 317 and senses a hydrogen ion concentration (pH). The sensing unit 340, as illustrated in FIGS. 17A to 17C, may include a reference electrode 341 and a plurality of sensing electrodes 343.

The reference electrode 341 may be formed to have the shape of a plate in such a manner as to cover the respective tops of the inlet port 313, the plurality of fluid channels 315, and the plurality of reaction chamber 317. The reference electrode 341 may be combined with the rear surface of the cartridge body 310. That is, the reference electrode 341 according to the third embodiment of the present disclosure may serve as the sealing member sealing the rear surface of the cartridge body 310.

The reference electrode 341 may include an electrode terminal surface 341a extending downward toward a bottom surface of the cartridge body 310 and may be electrically connected to the diagnosis module main body 400 through the electrode terminal surface 341a.

The reference electrode 341 has a surface that is brought into contact with the top of each of the plurality of reaction chambers 317. This surface may be brought into contact with the sample solution. The reference electrode 341 has predetermined reference potential that results from a change in a hydrogen-ion concentration (pH) of the sample solution. The reference electrode 341 may be formed of a half-cell reactive material that is stable to a range of pH and provides high reproducibility. For example, the reference electrode 341 may be formed of Ag/AgCl.

A half cell here means a cell in which a potential difference resulting from an oxidation half reaction or a reduction half reaction occurs. That is, when an oxidation reaction or a reduction reaction occurs according to a value of the hydrogen-ion concentration (pH) of the sample solution in each of the plurality of sensing electrodes 343, the reference electrode 341 may operate as a reduction electrode or an oxidation electrode that is different from the plurality of sensing electrodes 343.

Each of the plurality of sensing electrodes 343 is spaced apart from the reference electrode 341 and is brought into contact with the sample solution in the internal space in each of the plurality of reaction chambers 317. Each of the plurality of sensing electrodes 343 may be formed in a manner that passes through the cartridge body 310 in order to be positioned in the internal space in the each of the plurality of reaction chambers 317. That is, each of the plurality of sensing electrodes 343 may be formed in such a manner as to be inserted from the bottom surface of the cartridge body 310 into the internal space in each of the plurality of reaction chambers 317. Therefore, first end portions of the plurality of sensing electrodes 343 may be arranged in the internal spaces, respectively, in the plurality of reaction chambers 317 and may be brought into contact with the sample solution. Second end portions thereof may be exposed at the bottom surface of the cartridge body 310 and may be electrically connected to the diagnosis module main body 400.

Each of the plurality of the sensing electrodes 343 has sensing potential that varies with a change in the hydrogen-ion concentration (pH) of the sample solution. That is, the reference electrode 341 and both ends of each of the plurality of sensing electrodes 343 operate as a potential condenser. The sensing potential of each of the plurality of sensing electrodes 343 varies with respect to reference potential of the reference electrode 341. Each of the plurality of sensing electrodes 343 here may be formed of a metal oxide material sensitive to the hydrogen ion concentration (pH), for example, ITO, $SiO_2$, or the like.

The diagnosis module main body 400' may be detachably combined with the cartridge 300'. The diagnosis module main body 400' may supply heat at a predetermined temperature, which is necessary for the nucleic acid amplification reaction, to the cartridge 300' and may convert a change in the hydrogen ion concentration, which results from the nucleic acid amplification reaction, into an electrical signal. Thus, the diagnosis module main body 400' may determine whether or not the diagnosis target is present.

The diagnosis module main body 400', as illustrated in FIG. 18, may include a body 410', a heat supply module 420', a detection module 430', a power supply module 440', a sensing module 450', and an integrated control module 460'. The body 410' and the power supply module 440' have the same configurations as the body 410 and the power supply module 440, respectively, according to the first embodiment of the present disclosure, and thus detailed descriptions thereof are omitted.

The heat supply module 420' is detachably combined with the cartridge 300'. Under the control of the integrated control module 460', the heat supply module 420' supplies heat at a predetermined temperature, which is necessary for the nucleic acid amplification reaction, to each of the plurality of reaction chambers 317.

The heat supply module 420', as illustrated in FIG. 19, may include a thermal conductivity body 421' and a heating unit 423'. The thermal conductivity body 421' is inserted into the cartridge 300'. The thermal conductivity body 421' is supplied with heat at a predetermined temperature from the heating unit 423' and transfers the heat to the cartridge 300'.

The thermal conductivity body 421' may accommodate the cartridge body 310 and the heating unit 423 and may include the cartridge insertion groove 421a' and first and second connector insertion holes 421b' and 421c'. The cartridge insertion groove 421a' may be formed at a position corresponding to the insertion hole 411a in the lower body 411 and may be formed in such a manner that an inner surface thereof is brought into contact with a front surface, a rear surface, and a bottom surface of a portion of the cartridge body 310, the portion including the plurality of reaction chambers 317. The cartridge insertion groove 421a' may be formed in such a manner that a bottom surface thereof is stepped in a manner that corresponds to the electrode terminal surface 341a of the reference electrode 341.

The first connector insertion hole 421b' may be formed in a bottom surface of the cartridge insertion groove 421a' in a manner that passes through the cartridge insertion hole 421a' from top to bottom. The second connector insertion hole 421c' may be formed in the bottom surface of the cartridge insertion groove 421a' in a manner that is spaced apart a predetermined distance from the first connector hole 421b' and in a manner that passes through the cartridge insertion groove 421a' from top to bottom.

The heating unit 423' is arranged within the thermal conductivity body 421'. Under the control of the integrated control module 460', the heating unit 423' generates heat at a predetermined temperature. Example of the heating unit 423' may include a resistor heater, a thermoelectric element, or the like. The first embodiment of the present disclosure is not limited to this heating unit 423'. The heat supply module 420' may further include a cooling unit dissipating heat generated from the thermal conductivity body 421' to the outside, and the like.

The detection module 430' is electrically connected to a sensing unit 340' of the cartridge 300' and supplies a reference voltage of predetermined magnitude to the reference electrode 341. The detection module 430' measures a sensing voltage of each of the plurality of sensing electrodes 343 and generates a plurality of detection signals. The detection module 430' transmits the detection signal to the integrated control module 460'.

The detection module 430', as illustrated in FIG. 20A, may include a reference electrode connector 431', a plurality of sensing electrode connectors 433', a reference voltage supply unit 435, and a hydrogen-ion concentration detection unit 437. The reference electrode connector 431' is inserted into the first connector insertion hole 421b' in the thermal conductivity body 421' and is brought into contact with the reference electrode 341.

The reference electrode connector 431' has an insertion groove 431a into which the electrode terminal surface 341a of the reference electrode 341 is inserted, and may be brought into surface contact with the electrode terminal surface 341a. The third embodiment of the present disclosure is not limited to this shape of the reference electrode connect 431'. The reference electrode connector 431' may be bent in the form of ¬ and thus may be brought into contact with the electrode terminal surface 341a of the reference electrode 341.

The plurality of sensing electrode connectors 433' are inserted into the plurality of second connector insertion holes 421c', respectively, in the thermal conductivity body 421' and is brought into contact with the plurality of sensing electrodes 343, respectively. The plurality of sensing electrode connectors 433' may be brought into contact with the plurality of sensing electrodes 343, respectively, at the bottom surface of the cartridge body 310.

The reference voltage supply unit 435 supplies predetermined voltage potential to the reference electrode 341 through the reference electrode connector 431'.

The hydrogen-ion concentration detection unit 437 is electrically connected to the plurality of sensing electrodes 343 through the plurality of sensing electrode connectors 433', respectively. The hydrogen-ion concentration detection unit 437 detects the sensing potential of each of the plurality of sensing electrodes 343 and generates the plurality of detection signals.

The hydrogen-ion concentration detection unit 437 may include a plurality of non-inverting operational amplifiers (AP). Each of the plurality of non-inverting operational amplifiers (AP), as illustrated in FIG. 20B, may include a non-inverting input terminal (+), an inverting input terminal (−), and an output terminal. The non-converting input terminal (+) is connected to each of the plurality of sensing electrode connectors 433'. A ground voltage is applied to the inverting input terminal (−). The output terminal outputs a detection signal Vout.

According to a change in the hydrogen-ion concentration (pH) of the sample solution (SS), sensing potential Vs of the sensing electrode 343 may change by ΔVs from reference potential Vr. The non-inverting operational amplifiers (AP) may output an amount of the change in the sensing potential Vs as the detection signal Vout. That is, the hydrogen-ion concentration detection unit 437 may detect the change in the hydrogen-ion concentration (pH) of the sample solution within each of the plurality of reaction chambers 317 and may generate the detection signal Vout.

For example, from FIG. 21, it can be seen that, as indicated by C, a voltage level of the detection signal Vout changes according to the change in hydrogen-ion concentration. The third embodiment of the present disclosure is not limited to this change in the voltage level of the detection signal Vout. The reference electrode 341 may be formed of the material of each of the plurality of sensing electrodes 343, and conversely, each of the plurality of sensing electrodes 343 may be formed of the material of the reference electrode 341. In this case, it can be seen that, as indicated by D, the detection signal Vout changes in a direction opposite to a direction of the change in the hydrogen-ion concentration (pH).

The sensing module 450' may sense temperature of the heat supply module 420' and may generate a sensing signal. Then, the sensing module 450' may transmit the generated sensing signal to the integrated control module 460'. The sensing module 450' may include a temperature sensor.

The integrated control module 460' supplies heat at a predetermined temperature, which is necessary for the nucleic acid amplification reaction, to each of the plurality of reaction chambers 317 through the heat supply module 420'. The integrated control module 460' here may control the temperature of the heat supply module 420' in a manner that is uniformly maintained.

When the heat at the predetermined temperature is supplied to each of the plurality of reaction chambers 317, according to the plurality of detection signals, the integrated control module 460' finds out whether the diagnosis target is present. According to the plurality of detection signals, the integrated control module 460' may determine whether or not the hydrogen-ion concentration of the sample solution in each of the plurality of reaction chambers 317 changes. When the hydrogen-ion concentration changes, the integrated control module 460' may determine that the diagnosis target is present.

The integrated control module 460' may communicate with the user terminal 4 to transmit the result of diagnosing the diagnosis target. The integrated control module 460' may be controlled by the user terminal 4 and may be realized as a printed circuit board (PCB).

As described above, only with one integrated molecular diagnosis apparatus 1 or 3 according to the first or third embodiment of the present disclosure, a process from the pretreatment of the collected sample to the transmission of the result of the diagnosis can be performed. Therefore, the result of the diagnosis can be obtained simply and quickly. In addition, the result of the diagnosis can be obtained by employing an optical method or a method that uses an electrochemical sensor. Thus, the integrated molecular diagnosis apparatus can be simply manufactured in a small size and thus can be used for point-of-care testing. The result of the diagnosis can be obtained from the user terminal 2, and thus convenience can be improved.

Although the specific embodiment of the present disclosure has been described for illustrative purposes, those skilled in the art will appreciate that various modifications, additions and substitutions are possible, without departing from the scope and spirit of the disclosure as disclosed in the accompanying claims.

What is claimed is:

1. An integrated molecular diagnosis apparatus comprising:
a buffer tube into which a sample collection tool collecting a sample is inserted, the buffer tube preparing a sample solution that contains nucleic acid extracted from the collected sample;
a cartridge combined with the buffer tube and supplied with the sample solution, the cartridge transporting the sample solution to a reaction chamber through a fluid channel and performing a nucleic acid amplification reaction; and
a diagnosis module main body detachably combined with the cartridge, the diagnosis module main body supplying heat at a predetermined temperature to the reaction chamber, detecting the nucleic acid amplification reaction, and determining whether or not a diagnosis target is present,
wherein the cartridge comprises:
a cartridge body formed in the shape of a plate in such a manner to have a front surface and a rear surface; and
a cartridge holder combined with the front surface of the cartridge body, wherein the cartridge body comprises:
a tube accommodation body formed on the front surface of the cartridge body and having an internal space in which the buffer tube is inserted;
an inlet port formed in the rear surface of the cartridge body in a manner that passes therethrough at a support surface of the tube accommodation body that is brought into contact with a bottom surface of the buffer tube;
an outlet port formed in the front surface of the cartridge body and arranged between the inlet port and the reaction chamber;
the fluid channel formed in the rear surface of the cartridge body, the sample solution being transported along the fluid channel from the inlet port to the outlet port;
the reaction chamber formed within the fluid channel in the rear surface of the cartridge body, the reaction chamber accommodating the sample solution, containing a pre-injected reagent, supplied with the heat at the predetermined temperature, and performing the nucleic acid amplification reaction; and
an outlet-port plugging member inserted into the outlet port, the outlet-port plugging member allowing air to pass through and blocking passage of the sample solution.

2. The integrated molecular diagnosis apparatus of claim 1, wherein a buffer solution is pre-injected into the buffer tube, a cell membrane of the sample is destroyed by shaking the sample collection tool in a state of being inserted, and the nucleic acid is extracted.

3. The integrated molecular diagnosis apparatus of claim 2, the buffer tube comprises:
a tube body accommodating the sample collection tool and having an internal space in which the buffer solution is pre-injected;
an opening and closing body combined with the tube body and opening and closing the internal space; and
an inlet-port plugging member inserted into the opening and closing body in a manner that passes therethrough, moved by a pressing pressure applied from the diagnosis module main body, and selectively allowing air to be introduced into the inner space in the tube body.

4. The integrated molecular diagnosis apparatus of claim 3, wherein the opening and closing body comprises:
a protrusion jaw formed in the shape of a ring and protruding from a lower surface of the opening and closing body, an outer circumferential surface of the protrusion jaw being inserted into an inner circumferential surface of the tube body;
a through-hole formed in the opening and closing body in a manner that passes therethrough from an upper surface thereof to the lower surface thereof, the inlet-port plugging member being inserted into the through-hole; and
a plurality of vent holes formed in the lower surface between a lateral surface of the through-hole and the protrusion jaw and formed to be spaced apart from each other.

5. The integrated molecular diagnosis apparatus of claim 3, wherein the diagnosis module main body comprises:
a pressing member formed at a position corresponding to the inlet-port plugging member, and
wherein the pressing member applies the pressing pressure to the inlet-port plugging member by an operation of opening and closing the diagnosis module main body.

6. The integrated molecular diagnosis apparatus of claim 1, the buffer tube is formed of a plastic material containing at least one of polypropylene and polycarbonate.

7. The integrated molecular diagnosis apparatus of claim 1, wherein the fluid channel comprises:
a first flow path formed in such a manner as to extend from the inlet port to the reaction chamber; and
a second flow path formed in such a manner as to extend from the reaction chamber to the outlet port.

8. The integrated molecular diagnosis apparatus of claim 7, the second flow path is formed in such a manner as to be curved in a zigzag fashion.

9. The integrated molecular diagnosis apparatus of claim 1, the outlet-port plugging member is formed of at least one of porous polyethylene and porous hydrogel.

10. The integrated molecular diagnosis apparatus of claim 1, wherein the tube accommodation body comprises:
a combination hole formed in a front surface thereof; and
a hole drilling member formed in the support surface and drilling a hole in a bottom surface of the buffer tube.

11. The integrated molecular diagnosis apparatus of claim 10, wherein the cartridge holder comprises:
an elastic member formed on an inner lateral surface thereof that faces the tube accommodation body and elastically deformed with a sliding motion due to the insertion of the buffer tube; and
a combination protrusion formed in such a manner as to protrude from the elastic member at a position corresponding to the combination hole and having an inclined surface.

12. The integrated molecular diagnosis apparatus of claim 11, wherein the buffer tube has a concave groove formed in an outer surface thereof at the position corresponding to the combination hole,
wherein the combination protrusion is inserted into the combination hole and thus is hooked onto the concave groove for being combined therewith, and
wherein the combination protrusion is supplied with an elastic restoring force from the elastic member and presses the buffer tube.

13. The integrated molecular diagnosis apparatus of claim 1, wherein the cartridge comprises:
  a sensing unit sensing a hydrogen-ion concentration of the sample solution within the reaction chamber.

14. The integrated molecular diagnosis apparatus of claim 13, wherein the sensing unit comprises:
  a reference electrode brought into contact with the sample solution and having predetermined reference potential that results from a change in the hydrogen-ion concentration of the sample solution; and
  a sensing electrode spaced away from the reference electrode, brought into contact with the sample solution, and having sensing potential that varies with the change in the hydrogen-ion concentration of the sample solution.

15. The integrated molecular diagnosis apparatus of claim 14, wherein the reference electrode is formed of Ag/AgCl.

16. The integrated molecular diagnosis apparatus of claim 14, wherein the reference electrode is formed in the shape of a plate in such a manner as to cover a top of the reaction chamber, combined with the cartridge body, extending toward a bottom surface of the cartridge body, and thus having an electrode terminal surface electrically brought into contact with the diagnosis module main body.

17. The integrated molecular diagnosis apparatus of claim 14, wherein the sensing electrode is formed in a manner that passes through the cartridge body in order to be positioned in an internal space of the reaction chamber.

18. The integrated molecular diagnosis apparatus of claim 13, wherein the diagnosis module main body comprises:
  a detection module electrically connected to each of the reference electrode and the sensing electrode, detecting sensing potential of the sensing electrode, and generating a detection signal; and
  an integrated control module determining the change in the hydrogen-ion concentration of the sample solution according to the detection signal and determining whether or not the diagnosis target is present.

19. The integrated molecular diagnosis apparatus of claim 1, wherein the cartridge is formed of a transparent plastic material containing at least one of polypropylene, polycarbonate, and acrylic.

20. The integrated molecular diagnosis apparatus of claim 1, wherein the diagnosis module main body comprising:
  a body having an internal space of predetermined size and having a lower body having an insertion hole into which the cartridge is inserted and an opening and closing body combined with the lower body and thus opening and closing the internal space, the insertion hole being formed in an upper surface of the lower body;
  a heat supply module arranged in the internal space in the body and detachably combined with the cartridge through a cartridge insertion groove formed at a position corresponding to the insertion hole, the heat supply module supplying the heat at the predetermined temperature to the reaction chamber;
  a detection module arranged in the internal space in the body, the detection module emitting light to the reaction chamber, measuring color or a fluorescent magnitude of the sample solution and thus generating a detection signal; and
  an integrated control module arranged in the internal space in the body, the integrated control module determining from the detection signal a change in the color or the fluorescent magnitude of the sample solution due to the nucleic acid amplification reaction, and determining whether or not the diagnosis target is present.

21. The integrated molecular diagnosis apparatus of claim 20, wherein the detection module comprises:
  a light source emitting light to the reaction chamber; and
  a light detector measuring the color or the fluorescent magnitude of the sample solution to which the light is emitted and generating the detection signal.

22. The integrated molecular diagnosis apparatus of claim 20, wherein the integrated control module communicates with a user terminal to transmit a result of diagnosing the diagnosis target to the user terminal.

* * * * *